(12) United States Patent
Harnach

(10) Patent No.: US 11,393,563 B2
(45) Date of Patent: Jul. 19, 2022

(54) SYSTEM AND METHOD FOR COORDINATING CARE WITHIN THE HEALTH INDUSTRY

(71) Applicant: Care Coordination Systems, LLC, Akron, OH (US)

(72) Inventor: Bob Harnach, Akron, OH (US)

(73) Assignee: Care Coordination Systems, LLC, Akron, OH (US)

(*) Notice: Subject to any disclaimer, the term of this patent is extended or adjusted under 35 U.S.C. 154(b) by 530 days.

(21) Appl. No.: 16/514,626

(22) Filed: Jul. 17, 2019

(65) Prior Publication Data
US 2020/0303045 A1    Sep. 24, 2020

Related U.S. Application Data

(60) Provisional application No. 62/819,947, filed on Mar. 18, 2019.

(51) Int. Cl.
*G16H 10/60* (2018.01)
*G16H 40/20* (2018.01)
*G16H 40/67* (2018.01)

(52) U.S. Cl.
CPC .............. *G16H 10/60* (2018.01); *G16H 40/20* (2018.01); *G16H 40/67* (2018.01)

(58) Field of Classification Search
CPC ........ G16H 50/20; G16H 10/60; G16H 50/30; G16H 10/00; G16H 10/40; G16H 40/63;
(Continued)

(56) References Cited

U.S. PATENT DOCUMENTS

2006/0047537 A1* 3/2006 Brimdyr ................ G16H 15/00
                                                                705/2
2013/0282397 A1* 10/2013 Easterhaus ............ G16H 40/20
                                                                705/3
(Continued)

OTHER PUBLICATIONS

"Connecting Those at Risk to Care—The Quick Start Guide to Developing Community Care Coordination Pathways", Developed by: "Community Care Coordination Learning Network—The Pathways Community HUB Institute", Prepared for: Agency for Healthcare Research and Quality, Jan. 2016.
(Continued)

*Primary Examiner* — Joseph D Burgess
(74) *Attorney, Agent, or Firm* — Emerson, Thomson & Bennett, LLC; Roger D. Emerson; Peter R. Detorre

(57) ABSTRACT

The present disclosure is directed to a computerized method, system and software application for coordinating medical care through a Pathways Community Hub (HUB). A Pathways Community Hub is a network of care coordination agencies which focuses its mission towards reaching individuals within the community having the greatest risk-factors through the deployment of service providers such as community care coordinators. The Pathways Community Hub finds at-risk individuals in need of medical, health-related or social services, treats identified risk factors and measures a patient's risk status over time. The goal of the Pathways Community Hub is to achieve a reduction of risk among patients through open communication and collaboration among service providers including medical service providers and community-based organizations and to reduce the overall cost of medical, health-related and social services over time within a region.

19 Claims, 53 Drawing Sheets

(58) Field of Classification Search
CPC ........ G16H 20/10; G16H 20/30; G16H 40/67; G16H 50/70
See application file for complete search history.

(56) References Cited

U.S. PATENT DOCUMENTS

| | | | |
|---|---|---|---|
| 2014/0074509 A1* | 3/2014 | Amarasingham | G16H 50/70 705/3 |
| 2015/0221046 A1* | 8/2015 | Roy | G06Q 50/00 705/2 |
| 2018/0068084 A1* | 3/2018 | Navani | G06N 5/003 |

OTHER PUBLICATIONS

Jennie Bonney, MPH and Debbie I. Chang, MPH, Nemours Children's Health System, "Community Care Coordination Systems: Connecting Patients to Community Services", Feb. 2018.

* cited by examiner

Client's Name ..................................................  Date of Birth ..................

Community Care Coordinator ..................  Agency ..........................

Adult Education Pathway

Initiation
Client identifies educational need(s).

↓

Partner with client to establish/review educational goals. Document goal and desired outcomes.

↓

Assist client in registering for training or educational course:
- Gather necessary documentation for registration.
- Determine if client needs to take an assessment/placement exam and schedule exam date.

↓

Confirm that client is registered in class or training program and attends first class.

↓

Monitor client's progress with educational program.
- Confirm at least biweekly that client is attending classes and document progress.

↓

Completion
Confirm that client successfully completes stated educational goal:
- Course/class completed
- Training program completed
- Quarter/semester completed Record reason if Finished Incomplete: ..........................

Start date ..........

Educational goals ..........

Date of first class ..........

Check-in dates ..........

FIG. 4

Client's Name _____  Date of Birth _____

Community Care Coordinator _____  Agency _____

Behavioral Health Pathway

Initiation
Client with behavioral health issue(s)

Initiation date _____

1. Identify referral source.
2. Document behavioral health issue(s) (Describe below)

Referral Source
☐ Parent
☐ School
☐ Doctor
☐ Self-referral
☐ Other _____

Schedule appointment for appropriate level of service based on client's need.

Appointment date _____

Agency/provider _____

Completion
Client has kept three scheduled appointments. Monitor follow-up appointments with Medical Referral Pathway.

Kept appointment date _____

Kept appointment date _____

Kept appointment date _____

Describe behavioral health issue(s): _____
_____
_____
_____

Care coordination plans: _____
_____
_____
_____

Record reason if Finished Incomplete: _____
_____
_____
_____

Client's Name _____  Date of Birth _____

Community Care Coordinator _____  Agency _____

Employment Pathway

| Flow | Details |
|---|---|
| Initiation — Client is requesting assistance in obtaining a job. | Start date _____ |
| Partner with client to identify: 1. Education and work history • Previous work experience • Educational level completed • Employment goals (special training needed for desired job) 2. Barriers to employment (felony record, financial constraints, etc.) | Work history _____ Educational level _____ Employment goals _____ Barriers _____ |
| Care coordinator will work with client to confirm that résumé is completed. | Date résumé completed _____ |
| Care coordinator will work with client to monitor applications submitted for employment. | Dates applications submitted _____ |
| Completion — Client has found consistent source(s) of steady income and is employed over a period of 3 months. | 1 month _____ 2 months _____ Completion—3 months _____ Check-in dates _____ |

Record reason if Finished Incomplete: _____

Client's Name .................................. Date of Birth ..................

Community Care Coordinator .................. Agency ..................

Health Insurance Pathway

Initiation
Client needs health insurance.

Start date ..................

Assist client and/or family in completing forms as directed and submit to appropriate agency.

Date application submitted ..................

Confirm with agency that all forms have been received and have been completed properly.

Completion
Arrange followup within 2-6 weeks of application submission to confirm acceptance or denial of insurance.
- If denied, record reasons in client's record and refer client to other community resources.
- If accepted, document status, including insurance number, in client's record.

Date approved ..................

Insurance ..................

Number ..................

Record reason if Finished Incomplete (reason denied and referral made):
..............................................................
..............................................................
..............................................................
..............................................................
..............................................................

FIG. 11

| Client's Name | Date of Birth |
|---|---|
| Community Care Coordinator | Agency |

Housing Pathway

Initiation
Client and/or family is identified to be in need of affordable and suitable housing.

Start date _____

↓

Identify reason(s) housing is required: (check all that apply)
- ☐ Eviction
- ☐ Homeless
- ☐ Domestic violence
- ☐ Lead
- ☐ Fire/natural disaster
- ☐ Self-imposed (pets)
- ☐ Discrimination
- ☐ Safety issue(s)
- ☐ Too many for living space
- ☐ Financial
- ☐ Poor rental history
- ☐ Poor location for access to services
- ☐ Disability
- ☐ Other: _____

↓

Partner with client to contact appropriate housing organization and schedule an appointment to meet and discuss housing options.

Help client prepare for meeting with required documentation, child care, transportation, etc.

Appointment scheduled _____

Appointment kept _____

↓

Care coordinator confirms that client kept appointment with housing organization.

If client is placed on a waiting list for housing, obtain name and phone number of contact person to follow up with regarding status.

Contact person _____

Contact number _____

↓

Follow up with housing contact person at least biweekly to monitor housing progress.

Check-in dates _____

↓

Completion
Confirmation that client and/or family has moved into an affordable suitable housing unit for a minimum of 2 months.

Completion date _____

Record reason if Finished Incomplete: _____

Client's Name .................................................... Date of Birth ..................

Community Care Coordinator .................... Agency ..........................

Medical Home Pathway

Initiation
Client needs a medical home (an ongoing source of primary medical care).

Start date ..................

↓

Determine payment source for health care.

Payment Source:
☐ Medicaid
☐ Medicare
☐ Private Insurance
☐ Self-pay
☐ Other: ..................

↓

Find appropriate primary medical provider options for payment source.

Medical provider ..................

↓

1. Obtain release of information from client.
2. Assist family in scheduling appointment.
3. Provide education about the importance of keeping the appointment.

Date of initial appointment ..................

Education provided
☐ Yes   ☐ No

↓

Completion
Confirm that appointment was kept.

Date of kept appointment ..................

Record reason if Finished Incomplete: ..................

FIG. 16

Client's Name _____ Date of Birth _____

Community Care Coordinator _____ Agency _____

Medical Referral Pathway

Initiation
Client needs a health care appointment.
Document type of appointment needed – use codes.
(Only ONE code per Pathway)

Start date _____

Referral - Code _____

Educate client/family about the importance of regular health care visits and keeping appointments.

Education provided
☐ Yes ☐ No

Appointment scheduled with health care provider/clinic.

Appointment date _____

Completion
Verify with health care provider that appointment was kept.

Date appointment kept _____

Document how appointment was verified _____

Code Numbers for Medical Referral Pathway
1. Primary Care
2. Specialty Medical Care _____
3. Dental
4. Vision
5. Hearing
6. Family Planning
7. Mental Health
8. Substance Abuse
9. Speech and Language
10. Pharmacy
11. Other, please specify in record _____

Record reason if Finished Incomplete: _____

Client's Name .............................................. Community Care Coordinator ..............................................
Date of Birth .............................................. Today's Date .............................................. Agency ..............................................

STEP 2 - Ask the following questions:

1. Are you having problems getting your medications? ☐ Yes ☐ No
   If yes – why?
   ..............................................................................................................................
   ..............................................................................................................................

2. Do you have problems paying for your medications? ☐ Yes ☐ No
   If yes – what can you afford?
   ..............................................................................................................................
   ..............................................................................................................................

3. Are you having any side effects from your medications? ☐ Yes ☐ No
   If yes – describe:
   ..............................................................................................................................
   ..............................................................................................................................

4. Do you use more than one pharmacy to get your medications? ☐ Yes ☐ No
   If yes – please list all pharmacies:
   ..............................................................................................................................
   ..............................................................................................................................

Notes:
..............................................................................................................................
..............................................................................................................................

Provider Signature .............................................. Date ..............................................

Client's Name _____ Date of Birth _____

Community Care Coordinator _____ Agency _____

Pregnancy Pathway

Initiation
Any woman confirmed to be pregnant through a pregnancy test.

Start date _____
Education provided
☐ Yes ☐ No

↓

Provide pregnancy education.

Date of 1st PN appt. – set up by
☐ Client
☐ Care Coordinator

↓

Schedule appointment with prenatal care provider:
- Date of 1st prenatal appointment
- Estimated due date
- Concerns identified Prenatal care provider _____

Due date _____

↓

Check on woman's prenatal appointments at least monthly.

Concerns _____
_____
_____
_____
_____

↓

Completion
Healthy baby > 5 lbs 8 ounces (2,500 grams).
Document baby's birth weight, estimated age in weeks, and any complications.

Date of birth _____

Birth weight _____

Gestational age (weeks) _____

Record reason if Finished Incomplete: _____
_____
_____

Client's Name _____  Date of Birth _____

Community Care Coordinator _____  Agency _____

Social Service Referral Pathway

Initiation
Client needs a social service referral.
Document type of service needed - use codes. (Only ONE code per Pathway)

Start date _____

Code number _____

Education provided
☐ Yes  ☐ No

↓

Provide appropriate education and discuss the importance of keeping appointments.

↓

Appointment scheduled with social service provider.

Date of appointment _____

↓

Completion
Verify that client kept scheduled appointment.

Date of kept appointment _____

Document how appt. was verified _____

---

Code Numbers for Type of Service

1. Child Assistance
2. Family Assistance
3. Food Assistance/WIC
4. Housing Assistance
5. Insurance Assistance
6. Financial Assistance
7. Medication Assistance
8. Transportation Assistance
9. Job/Employment Assistance
10. Education Assistance 11. Medical Debt Assistance
12. Legal Assistance
13. Parent Education Assistance
14. Domestic Violence Assistance
15. Clothing Assistance
16. Utilities Assistance
17. Translation Assistance
18. Help Me Grow
19. Other _____

Record reason if Finished Incomplete: _____
_____
_____
_____

FIG. 24

Appendix C. Sample Demographic and Referral Form

Richland Community HUB
Sample Demographic Form
Pregnant Client

Date: _____  Referred by: _____

Client's Name: _____

Address: _____

Phone: _____  Alternate Phone: _____

Client's Date of Birth: _____  Gender: M   F

Insurance Provider/Number: _____

Reason for Referral: _____

_____

_____

Is Client Pregnant?   Y   N   Estimated Due Date: _____
                              Estimated Weeks: _____
                              Date of 1st Prenatal Visit: _____

Referral Received by: _____

Referral Assigned to: _____ on _____

Referral Outcome: _____

Appendix D: Sample Adult Checklist

Initial Adult Checklist

Visit Date: _____ Start: _____ End: _____ Visit Type: _____
Care Manager: _____
Name: _____ DOB: _____
Address: _____ Phone: _____
SSN: _____ Race: _____ Ethnicity: _____ Gender: ☐ M  ☐ F
Insurance _____ Medicaid Number: _____
Referral Date: _____ Emergency Contact Number: _____

YES  NO   Client Information

___  ___   Are you single?
           If no: 1-significant other, 2-married, 3-separated, 4-divorced, 5-widowed, 6-other
           _____

___  ___   Do you rent your home or apartment?
           If no: 1-own home, 2-live with relatives, 3-live with friends, 4-not from this area,
           5-homeless, 6-other _____

___  ___   Do you speak another language besides English at home?
           If yes, do you need a translator for appointments? _____

___  ___   Are you in school now?
           If no: 1-college graduate, 2-high school diploma, 3-GED, 4-dropped out of high school,
           5-other _____

___  ___   Are you interested in finding a job?
           If no: 1-employed, 2-on disability, 3-enrolled in a training program, 4-other _____

If disabled, what is the reason? _____

___  ___   Do you need help with transportation to appointments?
           What are you using now for transportation? _____

___  ___   Do you have children?
           If yes: How many? _____

How many children live with you? _____

Do any of your children have special needs? _____

___  ___   Do you need help with child care?

___  ___   Do you have any problems providing:
           1-housing, 2-food, 3-clothing, 4-utilities, 5-other? _____

___  ___   Do you have any legal issues? _____

FIG. 26

YES NO General Health
___ ___ Do you need health insurance for yourself?
If no: Health insurance: _____
___ ___ Do you need a family doctor?
If no: Family doctor's name _____
___ ___ Do you need a dentist?
If no: Dentist's name _____

If you don't have a family doctor, where do you get your care?
1-ER, 2-Urgent Care, 3-Walk-in Clinic, 4-Other _____

Previous illnesses: _____
_____

Previous surgeries and hospitalizations: _____
_____

Allergies: _____
_____

YES NO Current Medical Issues
___ ___ Are you currently being treated for any of the following conditions?
1-infections, 2-asthma, 3-chronic medical conditions, 4-mental health conditions,
5-mental retardation, 6-developmental disabilities or delays, 7-other: _____

___ ___ Are you taking any medicines?
1-prescribed by your doctor, 2-over the counter, 3-herbal or alternatives, 4-other _____
List all medications: _____

YES NO Safety and Emotional Health
___ ___ Do you use tobacco products?
___ ___ Does anyone smoke in your home?
___ ___ Do you drink alcohol?
___ ___ Do you use other substances?
___ ___ Are you stressed?
___ ___ Are you feeling depressed?
___ ___ Have you experienced emotional, verbal, or physical abuse?
___ ___ Do you have a working smoke detector?
___ ___ Are there any safety concerns in the home?
Describe: _____
___ ___ Is there a gun in the home? If yes, is the gun locked? Yes ___ No ___
___ ___ Are there any pets in the home?
___ ___ If children at home, ask: Do you read to your child(ren)?
If yes, how often? _____

FIG. 26 (CONT'D)

List all other agencies that you are working with now:

........................................................................................................................
........................................................................................................................
........................................................................................................................
........................................................................................................................
........................................................................................................................

NOTES

........................................................................................................................
........................................................................................................................
........................................................................................................................
........................................................................................................................

Please add the following Pathway(s): (Represents the request from the care coordination agency to the HUB to add pathways to the Care Coordination Plan and tracking. List of Pathways here represents local set.

- ___ Adult Education
- ___ Chemical Dependency
- ___ Depression
- ___ Employment
- ___ Family Planning
- ___ Family Violence
- ___ Health Insurance
- ___ Immunization Screening
- ___ Immunization Referral
- ___ Lead
- ___ Medical Referral ........................................................................
- ___ Medication Assessment
- ___ Medication Management
- ___ Pregnancy
- ___ Postpartum
- ___ Smoking Cessation
- ___ Social Service Referral ........................................................................
- ___ Suitable Housing
- ___ Other: ........................................................................

Next home visit date: ........................................................................

FIG. 26 (CONT'D)

| Primary Care Provider | Nurse Practitioner (ARNP) or appropriate RN (BSN) | Master Social Worker (MSW) |
| --- | --- | --- |
| Community Health Worker (CHW) / Navigator | Pharmacist | Behavioral Health Provider |
| Primary Care Medical Home Representative | EMS / Paramedics | Nutritionist |
| MSS / Health Homes / TBD | Criminal justice stakeholder | Payer-based Clinician and/or MCO Case Manager |

HET Care Team member review meetings every two weeks includes the Primary Care, Pharmacist and Behavioral Health Provider to review care plan and progress.

Multiple HET Care Teams may be facilitated, simultaneously, in differing initiatives with different team composition and specializations.

FIG. 28

Local Events Calendar

* Add events
* Approve and publish events as the administrator
* Events are searchable
* Events and details are viewable online
* Request more information
* RSVP or reservations may be made via HealthBridge.care™

2

SYSTEM AND METHOD FOR COORDINATING CARE WITHIN THE HEALTH INDUSTRY

I. BACKGROUND

A. Field

The present disclosure generally relates to a method of coordinating care within the health industry, related processes and software applications.

B. Description of the Related Art

In the past, coordinating medical care typically involves the patient taking the initial responsibility to contact various medical, health-related and social service providers to obtain treatment for one or more conditions. Once a patient visits a particular service provider, the service may provide a referral to visit another service provider. The patient would then again have to contact the referred service provider for an appointment. This process has several inherent flaws. First, records related to the patient's condition are typically not shared among service providers. Also, there is often a lack of communication among service providers, especially over time as service providers change and medical records get lost. Treatments are often carried out moment by moment in a disjointed fashion. There very often is no a goal-oriented treatment plan to address the patient's needs. This often results in repeat visits and second opinions creating a burden on the patient seeking treatment and on individuals within the health industry. All of this leads to significant costs within the health industry for treating individuals whose needs are not being properly addressed. What is needed is a system and method to coordinate care within the health industry that addresses these issues.

II. SUMMARY

Provided is a system for coordinating medical care. The system includes the following components: a hub computing device which operates as a hub portal comprising a processor, a display and a non-transitory computer-readable storage medium containing a set of instructions encoded thereon, the instructions including: a data collection component, wherein the data collection component allows for a listing of clients or patients including client information and referral information, a listing of medical, health and social service providers to be uploaded onto the hub portal by the hub user and for recording of a patient's community health records with various service providers through use of the system; a health bridge referral component which allows the hub portal user to receive a request for a patient referral from a service provider, to access the patient's account, to conduct a search of service providers through a search engine, to select a service provider and add the type of referral requested; a first monitoring component which allows the hub portal user to enter a patient's account for a referral and view information associated with the patient within the account and which allows the hub portal user to monitor electronic communications between the patient and a service provider for particular patient referrals; a patient account status component which allows the hub user to monitor a patient's status of treatment within a particular pathway and which allows the hub user the ability to close a patient's account upon completion of a patient's treatment or pathway; and an archiving component which allows a hub user to move a particular referral or pathway to a historic tab upon completion of a patient's treatment or pathway; a measure, process and data display component wherein data related to a patient's community health record is run through artificial intelligence learning processes to analyze the data and generate an output of recommendations for further pathway referrals and/or treatments; a plurality of client computing devices including: a processor, a display and a non-transitory computer-readable storage medium containing a set of instructions encoded thereon, the instructions including: a search engine component, wherein the search engine component returns a number of hits of medical, health or social service providers within a selected region upon the user entering a query within the search engine; a messaging component which allows the user to send an electronic message to an organization selected from a list of service providers obtained from the search engine query to request an appointment to obtain community services; a scheduling component which allows for appointments to be created between the patient and the service provider; a confirmation component which allows the service provider to confirm receipt of the appointment request or referral, wherein the hub computing device is directly linked to the client devices and communicatively coupled to the client devices through a network connection.

According to certain aspects of the present disclosure, the system includes an appointment feedback component which provides notice to a third party referring the patient for an appointment with a service provider that the appointment was kept.

According to further aspects of the present disclosure, the system includes a health record integration component which allows a patient's medical records or electronic health record with a medical service provider to be uploaded and merged with the patient's community health record established with various service providers through use of the system.

According to further aspects of the present disclosure, the messaging component allows for multi-user, real-time communications between the patient and the service provider.

According to further aspects of the present disclosure, the system includes a second monitoring component which allows health care providers to monitor electronic communications between the patient and community service providers within the system.

According to further aspects of the present disclosure, the system includes a direct messaging component which allows patients to communicate with service providers confidentially in a secure environment within the system.

According to further aspects of the present disclosure, the system includes a tracking component wherein community health records are entered into a patient's account within the system through completed Pathway forms which track the outcomes performed by the service provider.

According to further aspects of the present disclosure, the archiving component allows for recording and storing of patient community health records related to service visits, general patient records and general data entry related to the specific services provided.

According to further aspects of the present disclosure, the system includes an auto-invoicing component, wherein the auto-invoicing component works in conjunction with the archiving component to automatically generate bills for services provided to the patient.

According to further aspects of the present disclosure, the auto-invoicing component is performance-based in that it takes into account a patient's successful completion of pathways with the service provider in generating bills.

According to further aspects of the present disclosure, the measure, process and data display component runs artificial intelligence learning processes analyzing multiple patient data within a particular region and outputs data directed to health related trends within a particular region, wherein the measure, process and data display component further analyzes which pathways provide the most successful outcomes for individuals with certain conditions in a particular region, determines the factors that cause poor health outcomes within a community, determines which pathways are likely to provide the most successful outcomes for individuals having certain conditions in a particular region and provides pathway recommendations for individuals within a particular region.

According to further aspects of the present disclosure, the system includes a referral resource ranking component wherein the hub user and service providers are provided a curated list of referral resources that are ranked according to performance and curated and maintained by HUB operations.

According to further aspects of the present disclosure, a specific standardized pathway is identified and assigned to the patient for each risk factor identified by the service provider.

According to further aspects of the present disclosure, a reduction in risk is recorded and tracked by the completion of pathways.

According to further aspects of the present disclosure, in the event that a pathway which is not completed or a desired outcome is not reached for a given patient, the pathway is closed by marking it "finished incomplete", and wherein the service provider documents the reasons why the pathway was not successfully completed and records this data within the patient account within the system.

According to further aspects of the present disclosure, pathway incompletion data is monitored and tracked by the hub computing device and wherein the hub computing device compiles a list of reasons why pathways are "finished incomplete".

According to further aspects of the present disclosure, the hub computing device conducts a community needs assessment.

According to further aspects of the present disclosure, the hub user creates agreements with community-based organizations or agencies to delineate expectations around hiring, training and supervision of service providers employed with such community-based organizations or agencies.

According to further aspects of the present disclosure, the hub user, service provider, community-based organization or agency designates specific learning modules or training videos for the patient to view within the system.

According to further aspects of the present disclosure, patient engagement is tracked within the system and notifications concerning the patient's engagement is transmitted to all financial stakeholders.

III. BRIEF DESCRIPTION OF THE DRAWINGS

FIGS. 4 through 24 are examples of various Community Hub Pathways.

FIG. 25 is a sample demographic and referral form.

FIG. 26 is a sample Adult Checklist.

FIG. 28 is a chart showing an example community hub health engagement team.

IV. DETAILED DESCRIPTION

Figure 1:
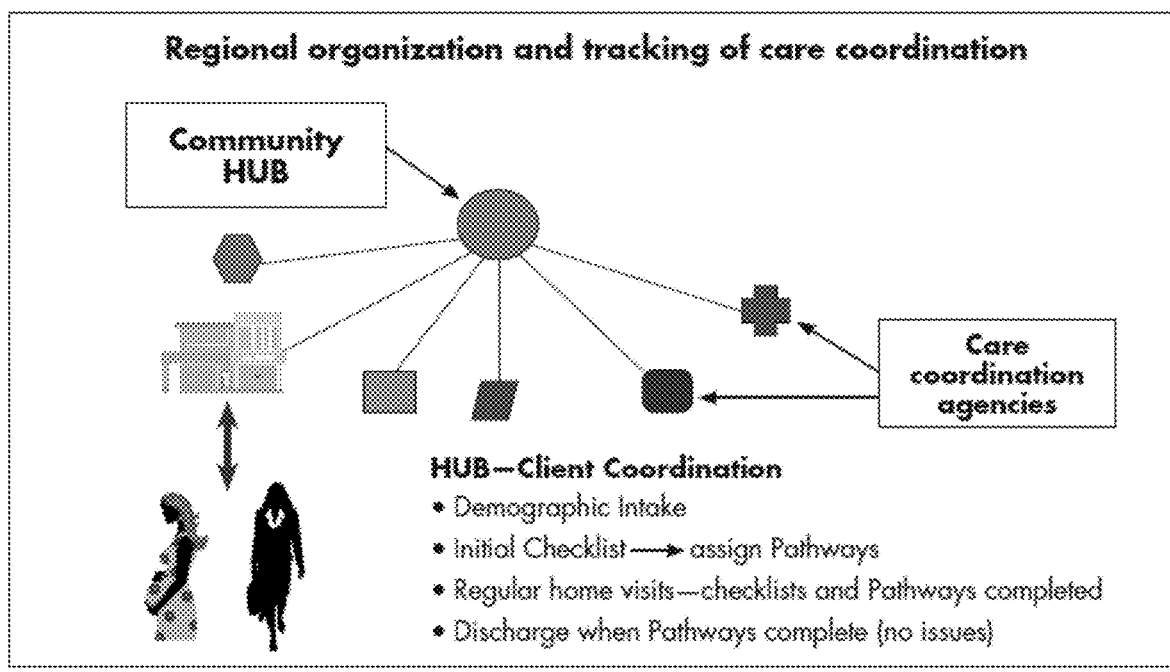
FIG. 1 is a diagram showing the regional organization and tracking of care coordination.
Figure 2:
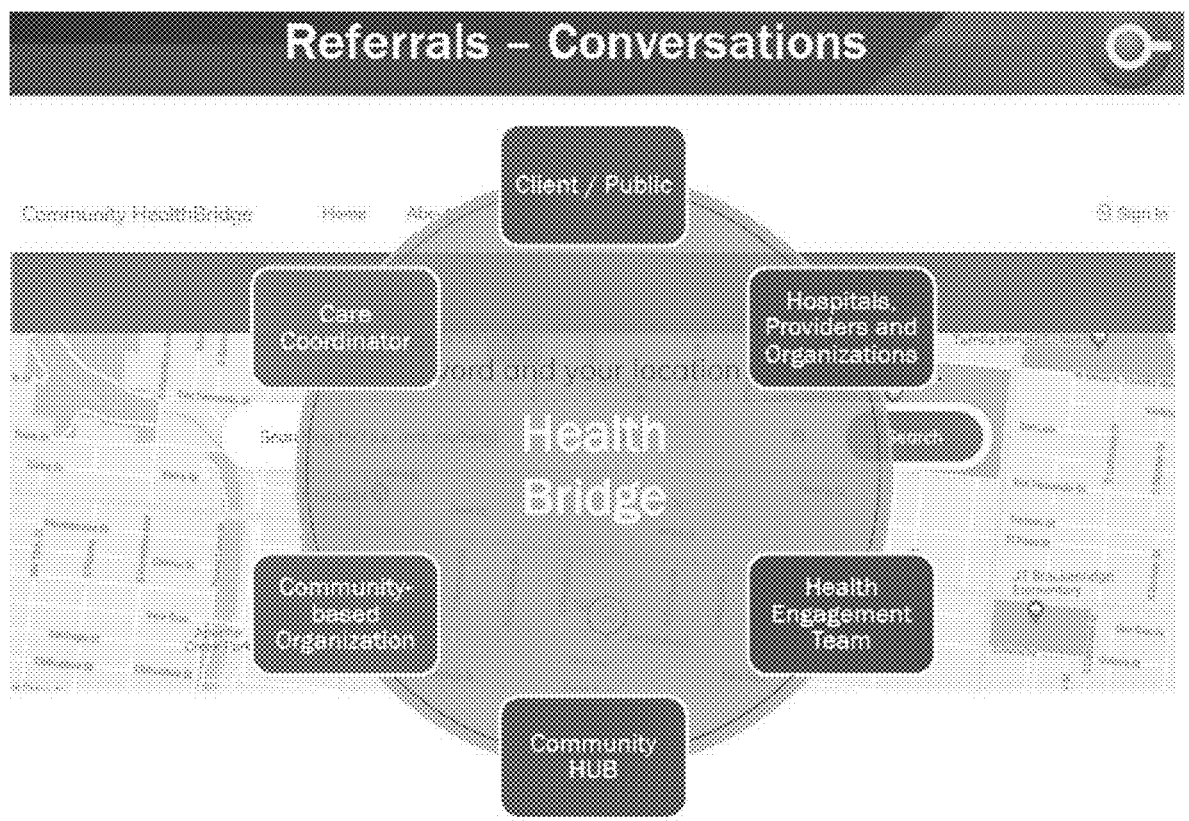
FIG. 2 is a diagram showing how the health bridge connects various parts of the coordinating care system.
Figure 3:
FIG. 3 is a diagram showing the interconnection of the parties of the coordinating care system.

Provided is a method for creating, using and managing a Pathways Community Hub. A Pathways Community Hub is a network of care coordination agencies which focus their mission towards reaching individuals having the greatest health-related and socio-economic risks, identifying associated risk factors and addressing identified risk factors of such individuals. Care coordination agencies typically represent any agency which deploys community care coordinators (CCCs). Community care coordinators include community health workers, nurses, social workers and others which reach out to individuals within the community and assist them connect with needed care. Care coordination agencies include local community organizations, outreach centers, health departments and care coordinators who are part of a community health center.

The Pathways Community Hub (HUB) is operated by a Hub Agency which leads the network of care coordination agencies and develops contracts and requirements for care coordination agencies to participate within the HUB. Pathways Community Hubs must adhere to certain national standards. Central Hub Agencies obtain national HUB certification through the Pathways Community HUB Institute (HUB Institute). The central Hub Agency ensures that these national standards are adhered to and are built into the accountability, function and billing process for the hub network.

Communities considering this model need to complete, or have access to, a thorough, up-to-date community needs assessment to determine the population of interest. Examples of recommended strategies for the assessment process include geocoding of health and social data, risk-scoring methodology, screening tools, and key stakeholder surveys that encompass at-risk community members. When the HUB is operational, strategies must be developed not only to "find" the at-risk individuals, but also to engage them in care coordination services.

The HUB is a neutral entity that does not directly provide care coordination services. Rather, the HUB gathers multiple care coordination agencies together into an organized team, trains and supports them to identify those in the community who are at the greatest risk and assesses and tracks each modifiable risk with standardized pathways for treatment. As noted, the HUB does not hire or deploy care coordinators but rather supports, coordinates and tracks outcomes for all agencies that provide direct on-the-ground, community-based care coordination.

When in use, a Pathways Community HUB provides the following three basic services: 1) Finds at-risk individuals in need of medical, health-related and/or social services. 2) Treats the risk-factor identified within the individual patient, and 3) Measures an individual's or patient's risk status over time.

As mentioned above, the HUB model includes a network of agencies that deploy community care coordinators to engage at-risk individuals in a pathways-focused care coordination. By pathways focused, it is meant that a set of treatments are identified for the patient to follow towards wellness.

New clients may be obtained or discovered through referrals or community outreach programs. When referrals for new clients are obtained, the community care coordinator completes all of the required paperwork to protect personal health information and submits it to the HUB. This step is completed before the client is registered as a new client within the HUB. One role for the HUB is to monitor and notify community care coordinators of any duplication of service. Once engaged, the community care coordinator and the patient are linked in the HUB. This allows the HUB to flag further attempts to register the patient for care coordination services. In certain cases, it is permissible for an at-risk patient to have more than one care coordinator, however, the reasons behind this type of decision need to be made clear.

For each risk factor identified by the community care coordinator, a specific standardized Pathway is assigned, and then each Pathway is tracked step by step through completion by the HUB. An at-risk individual may have many Pathways being addressed simultaneously, reflecting multiple health and social issues identified by the community care coordinator. The completion of each Pathway ensures the delivery of one or more evidence-based or best practice interventions to address the risk factor.

Pathways are the standardized outcome measurement tools the HUB tracks. As risk factors are identified and addressed, the Pathways are completed and a reduction in risk is recorded. HUBs need to have the capacity to measure and track an individual's risk status over time. HUBs may identify and treat risk reduction in specific areas, such as health, behavioral health, social factors, and financial security. Data obtained from such Pathways may be used to study the impact of care coordination over time. One element employed by the HUB to effectuate health system transformation is an intense focus on what factors are actually causing the poor health outcomes in a community and how these factors can be addressed most quickly and cost effectively.

The effectiveness of Pathways used both as a single measure and as a comprehensive group of measures has been tested and researched. The model and its impact affirm that like many other effective interventions that require more than one component, more than one risk factor must be addressed to demonstrate changes in health outcomes. A comprehensive assessment and multiple Pathways are employed to achieve a positive outcome. The measurement of specific items within the Pathways and multiple specific Pathways was conducted by Westat as part of a National Institutes of Health initiative.

Figure 13:
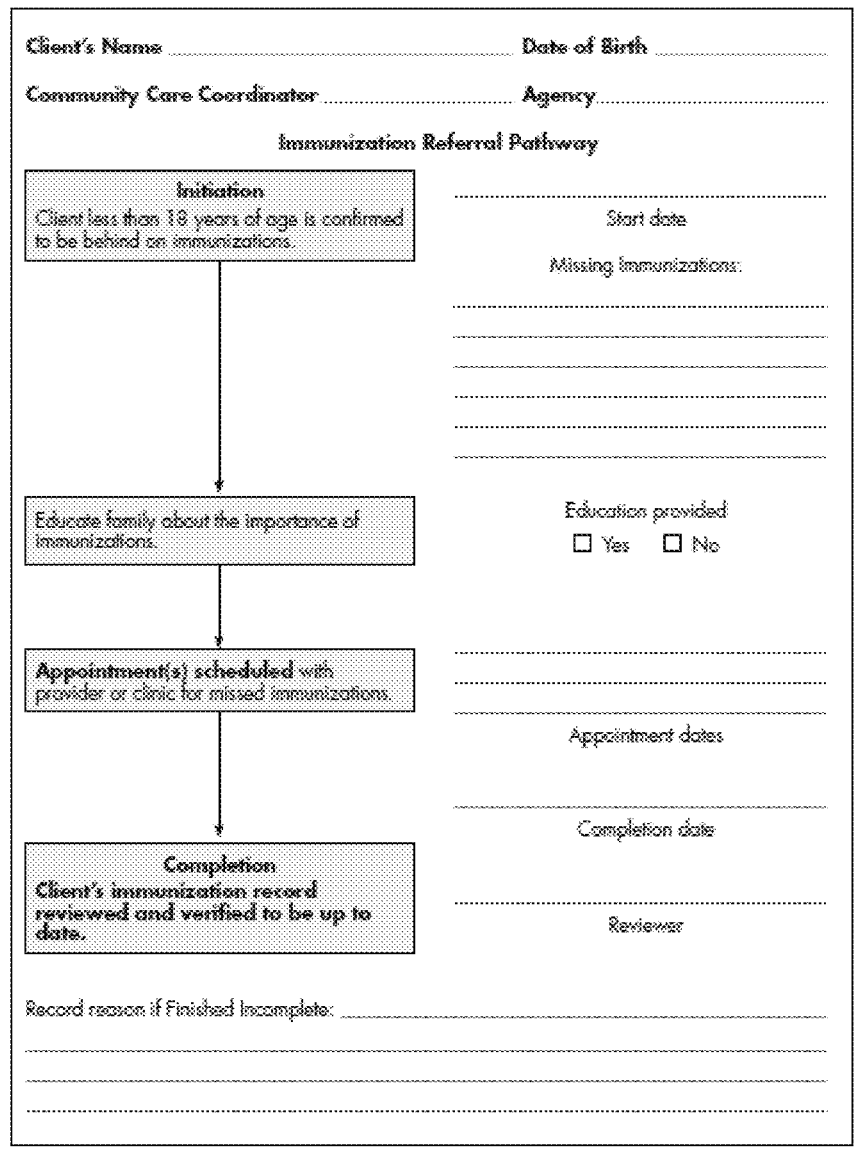
Figure 20:
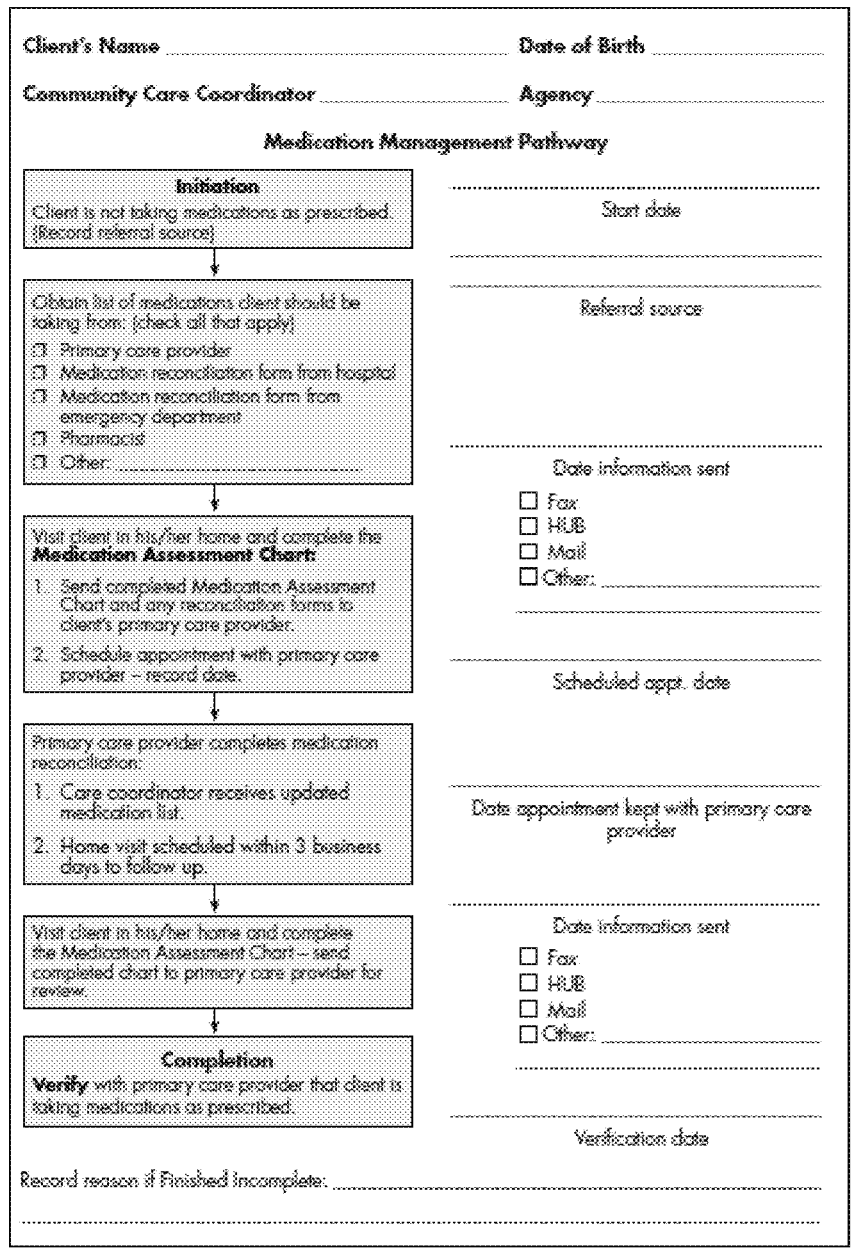
Figure 27:
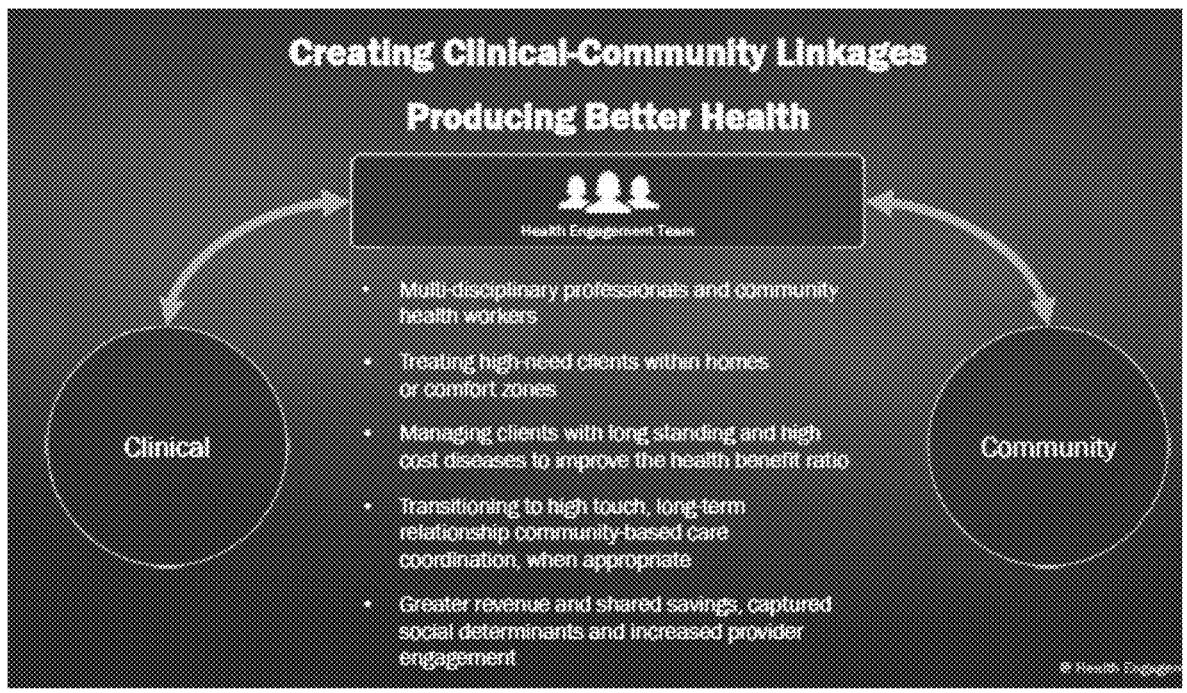
FIG. 27 is a diagram showing how a health engagement team creates a clinical-community linkage to produce better health among patients.
Figure 29:
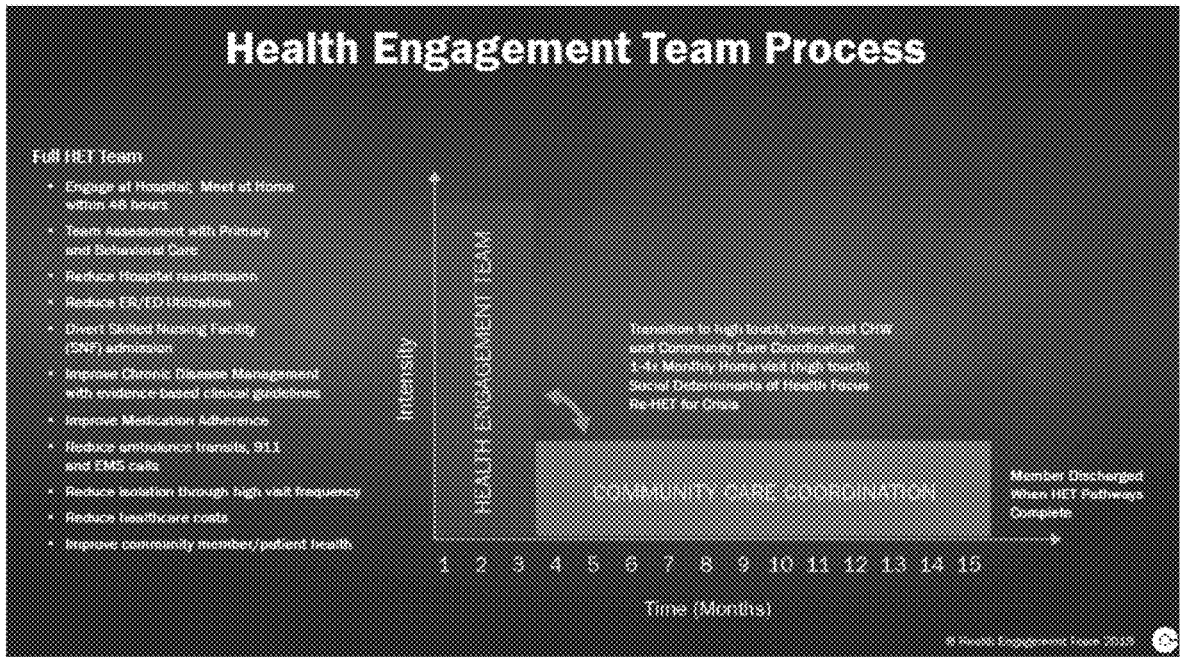
FIG. 29 is a chart illustrating the health engagement team process.
Figure 30:
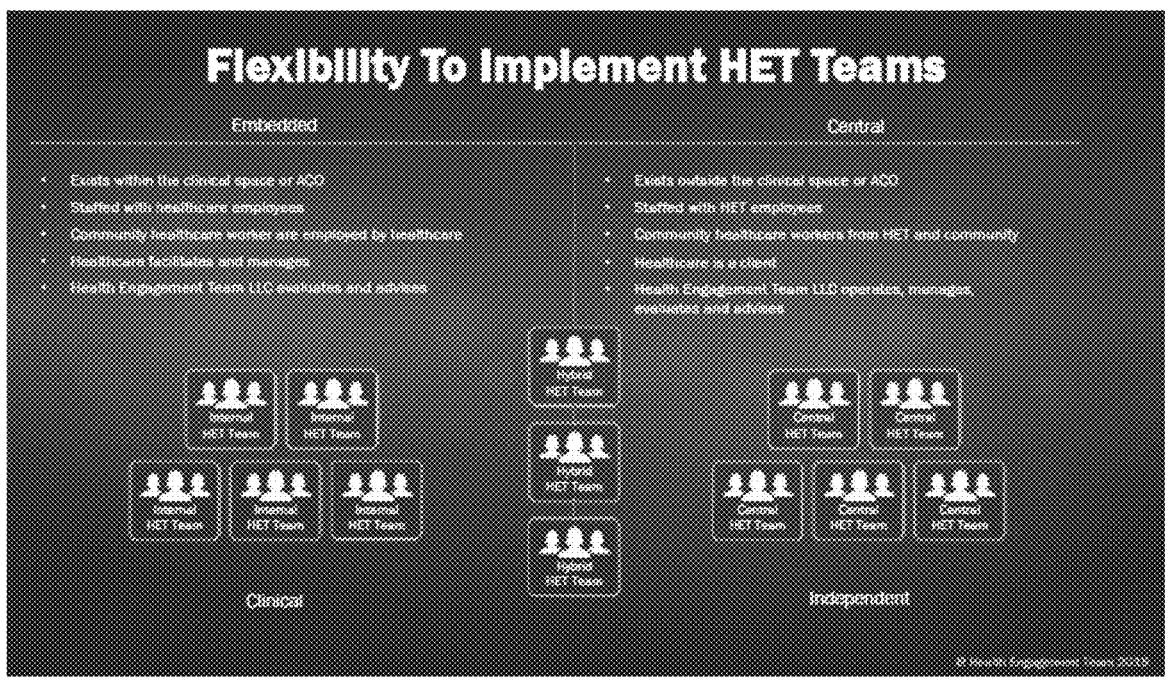
FIG. 30 is a chart illustrating the flexibility with implementing health engagement teams.
Figure 31:
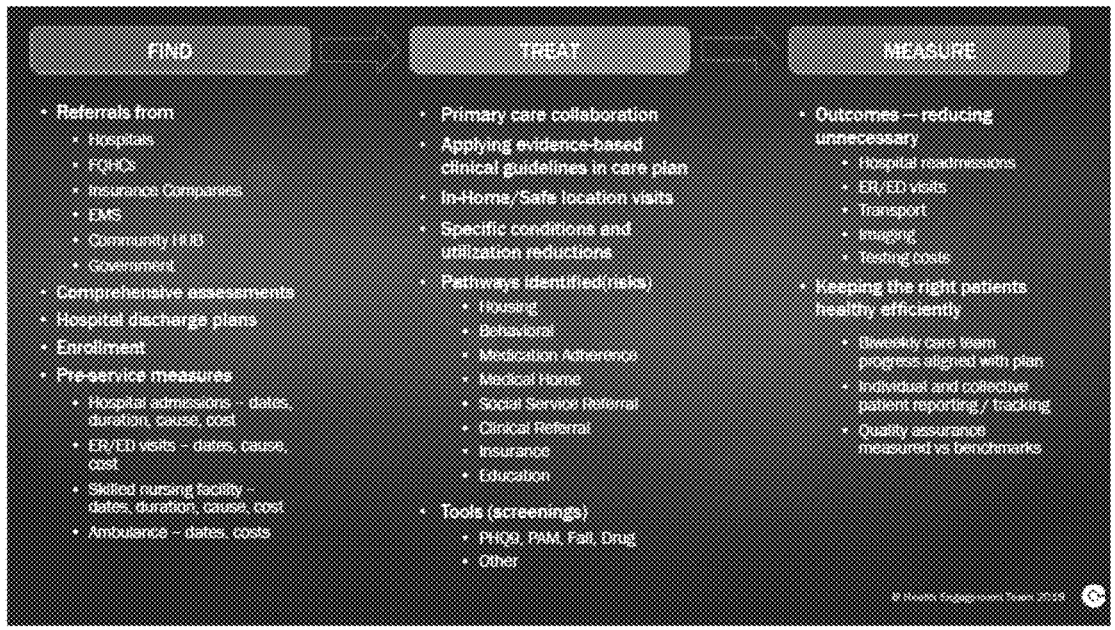
FIGS. 31 and 32 are charts illustrating the find, treat, measure activities of the Pathways Community HUB model.
Figure 32:
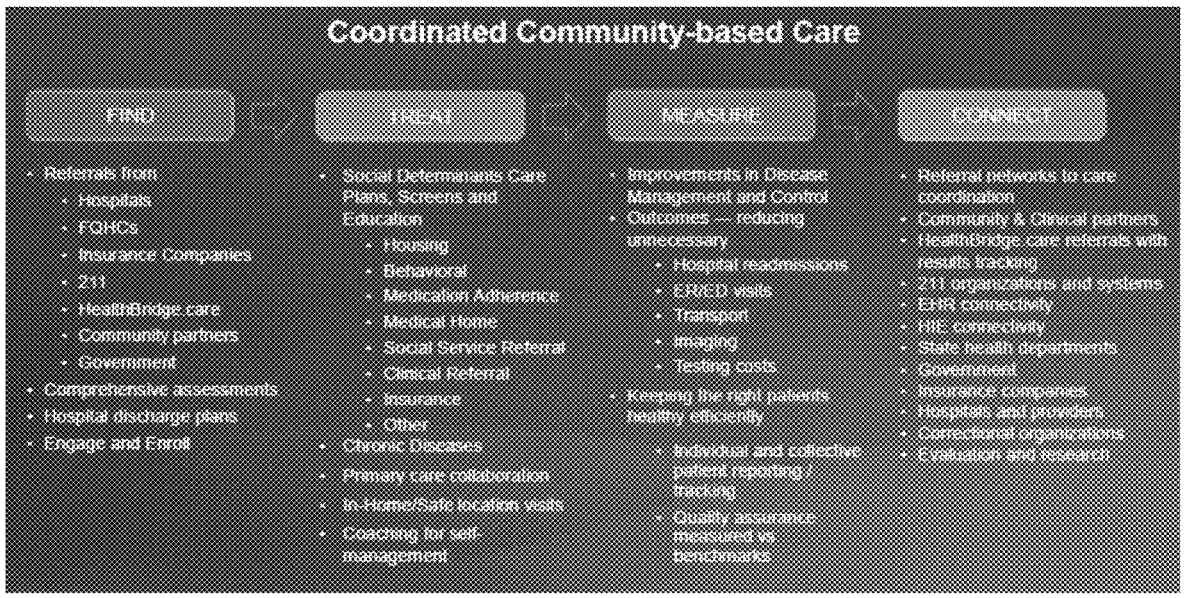
Figure 33:
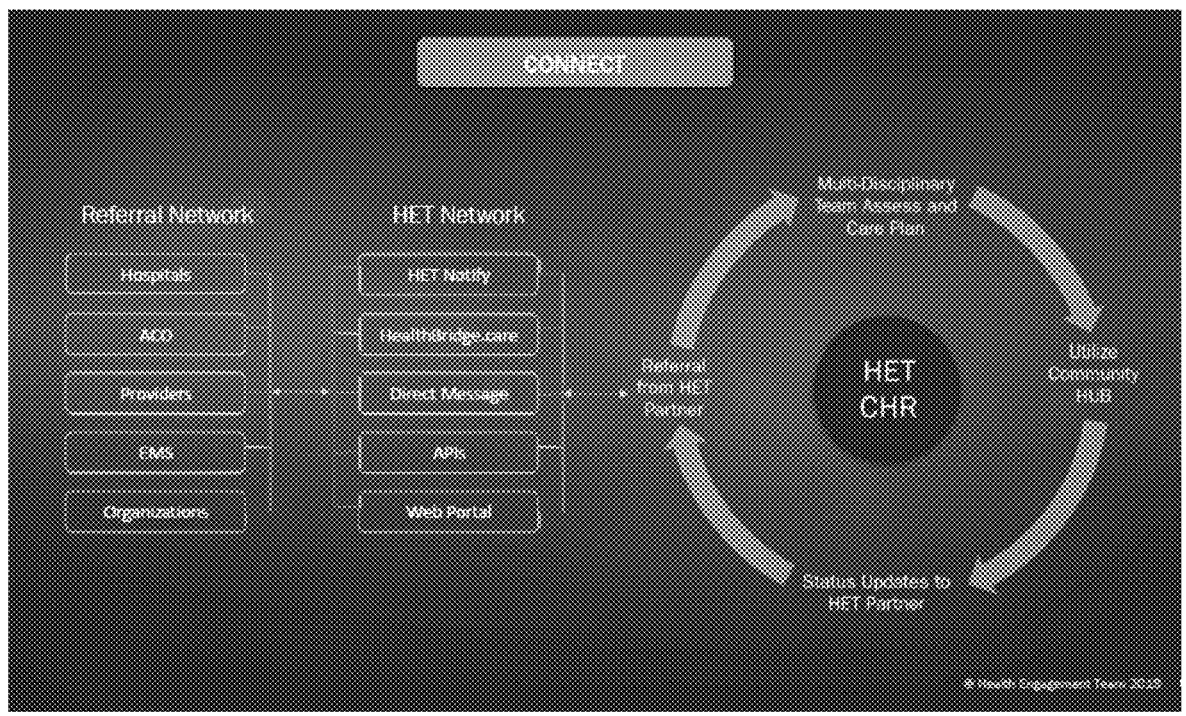
FIGS. 33 and 34 are diagrams showing how the health engagement team connects the referral network with the Pathways Community HUB.
Figure 34:
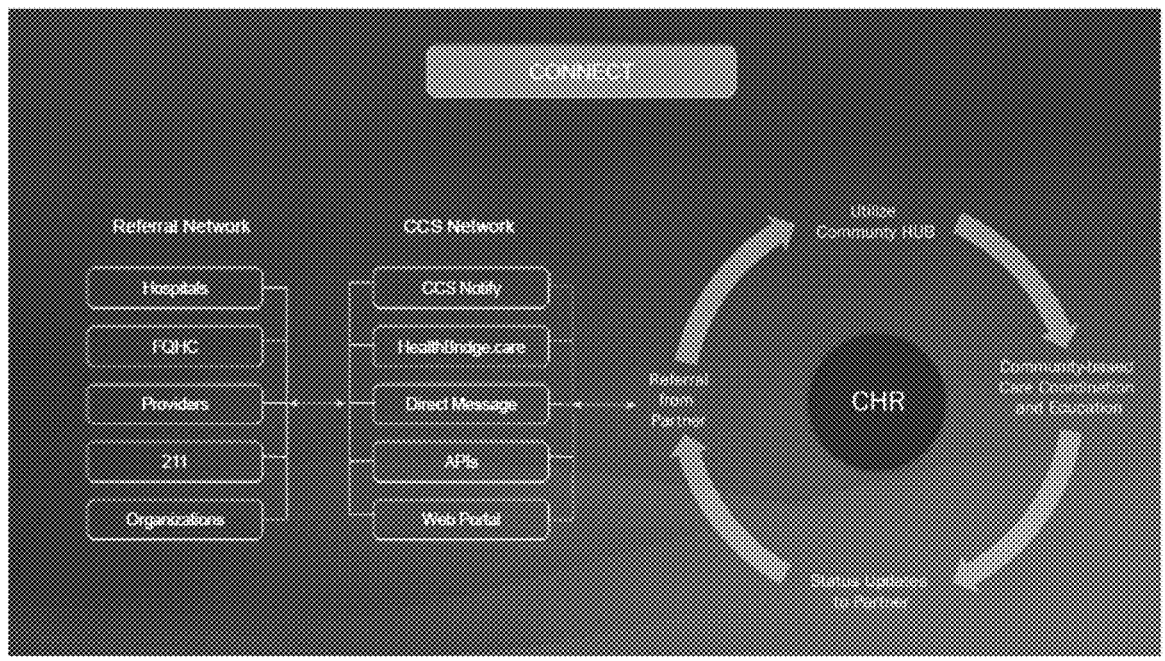
Figure 35:
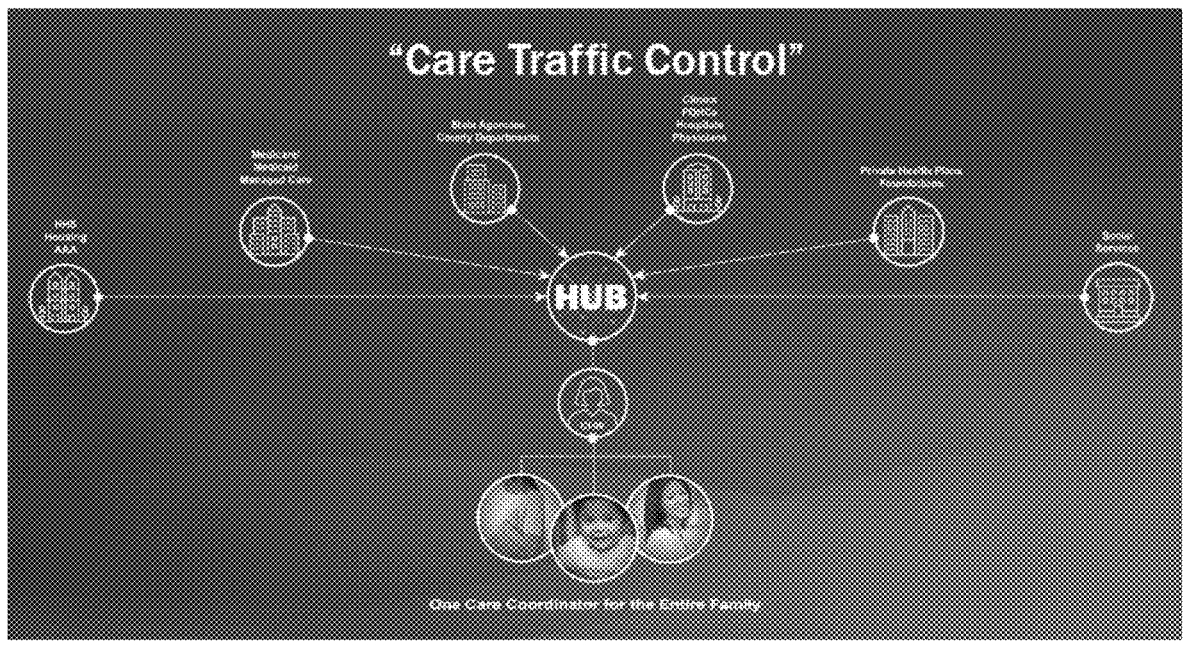
FIG. 35 is a diagram showing how the HUB connects the Community Health Worker with various organizations.
Figure 36:
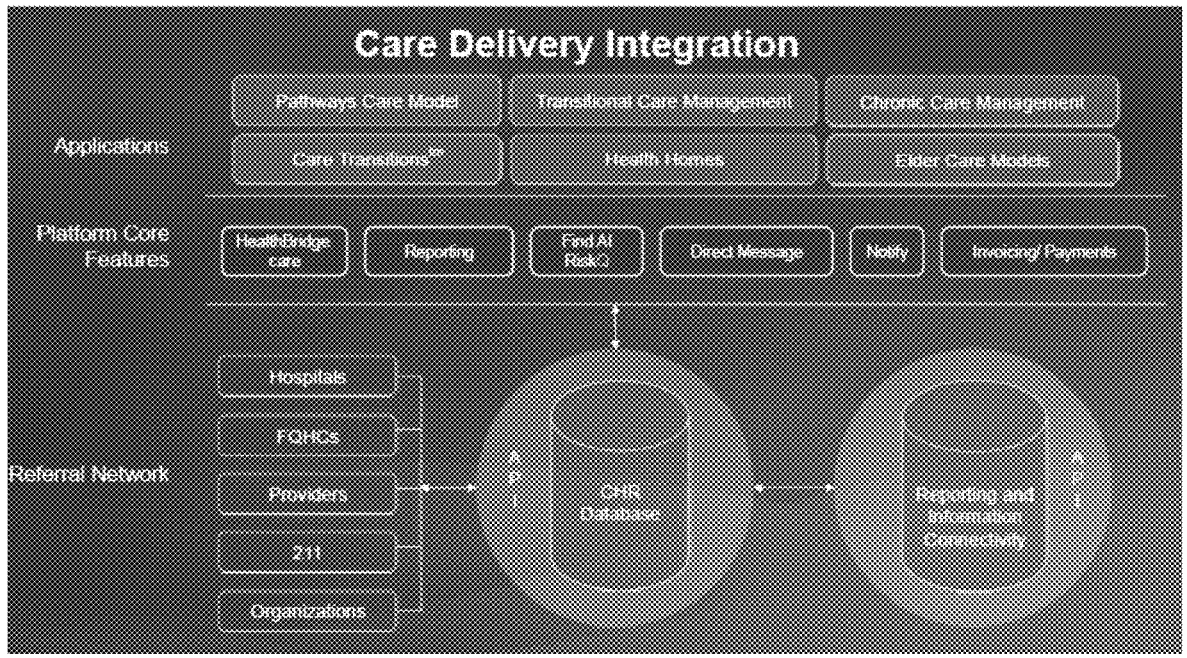
FIG. 36 is a diagram showing the integration of care delivery through the health engagement team.
Figure 37:
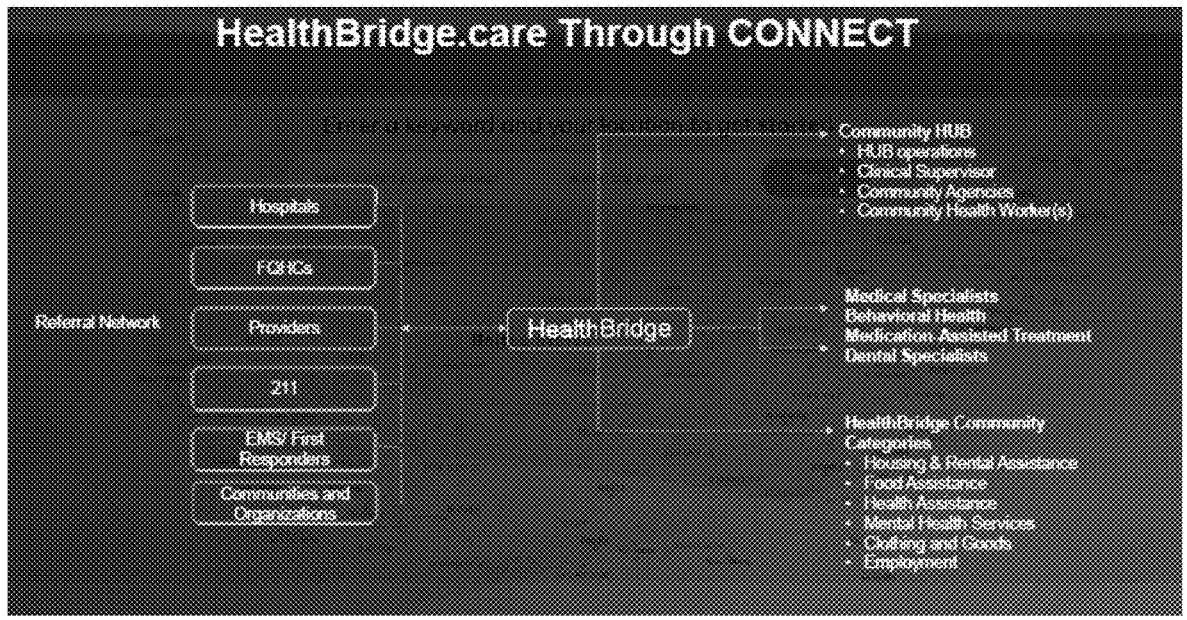
FIG. 37 is a diagram showing how the healthbridge connects the referral network with the health engagement team, medical and dental providers and providers within community based-organizations.
Figure 38:
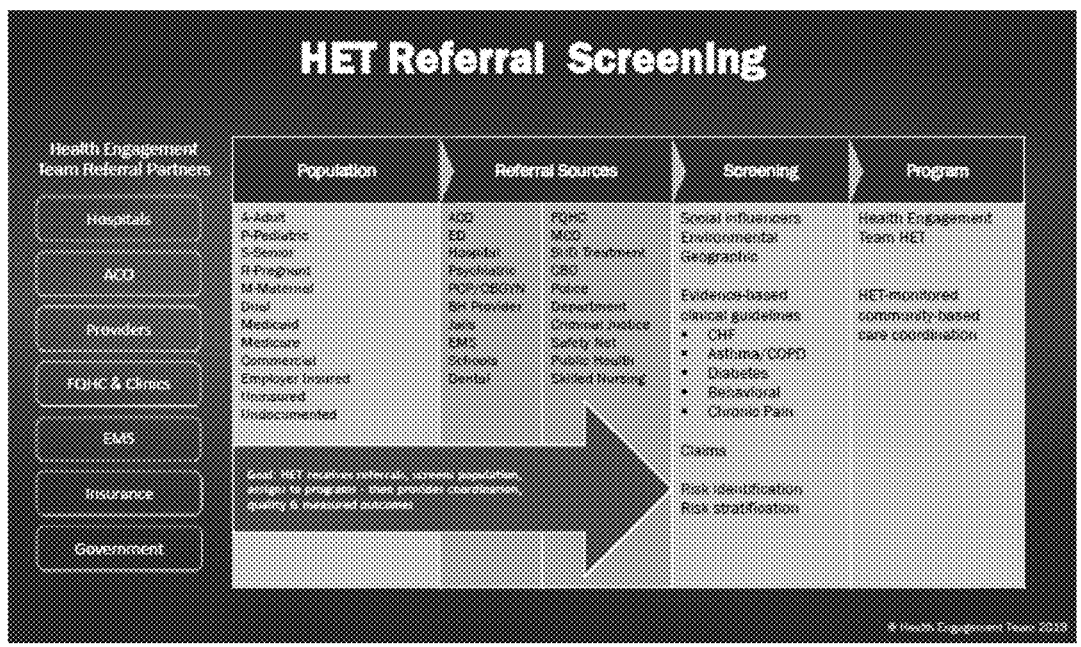
FIG. 38 is a chart illustrating the health engagement team screening process.
Figure 39:
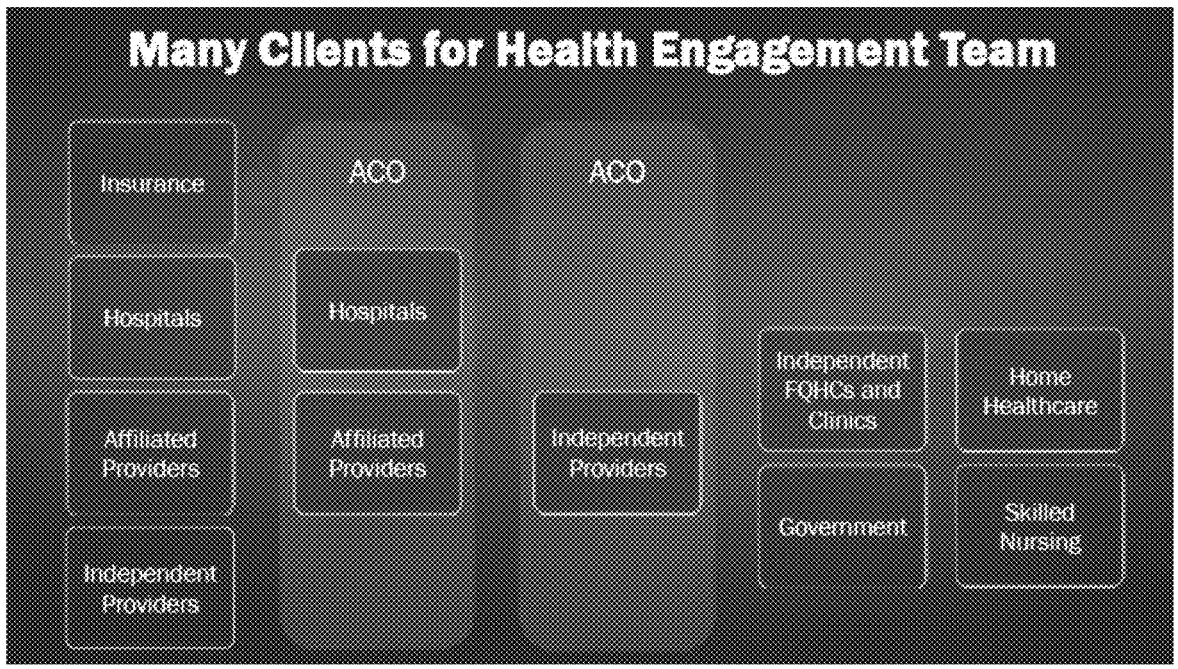
FIG. 39 is a chart listing the clients of the health engagement team.
Figure 40:
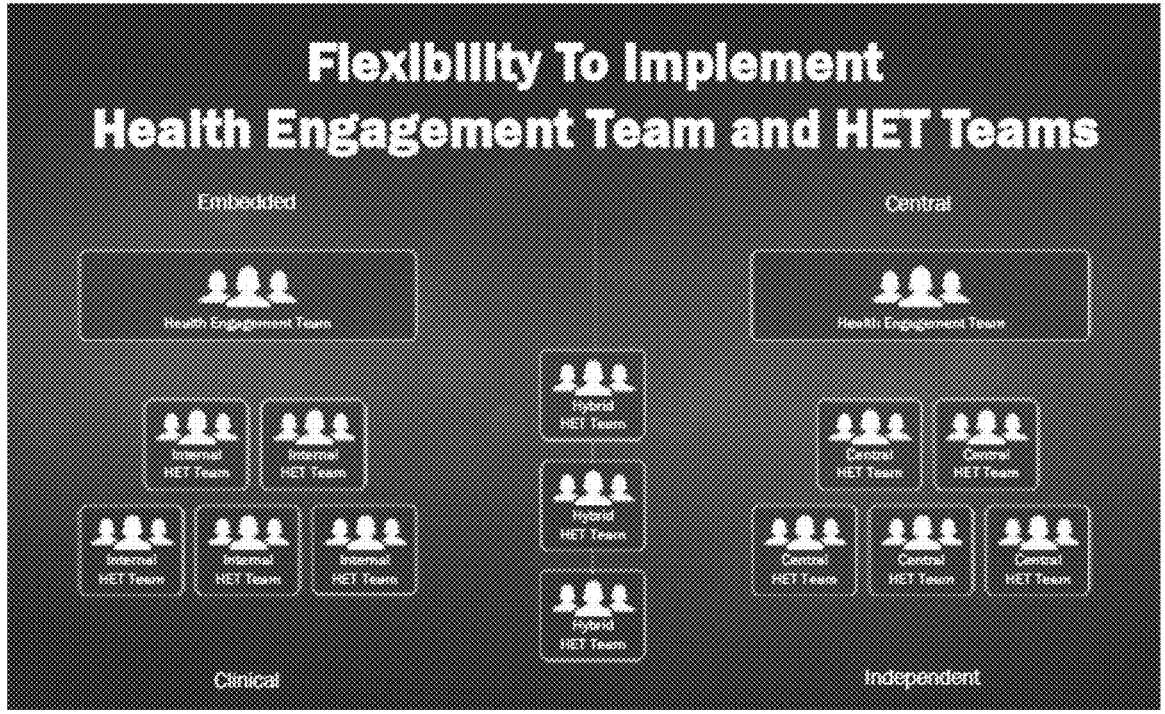
FIG. 40 is a chart illustrating options for implementing a health engagement team.
Figure 41:
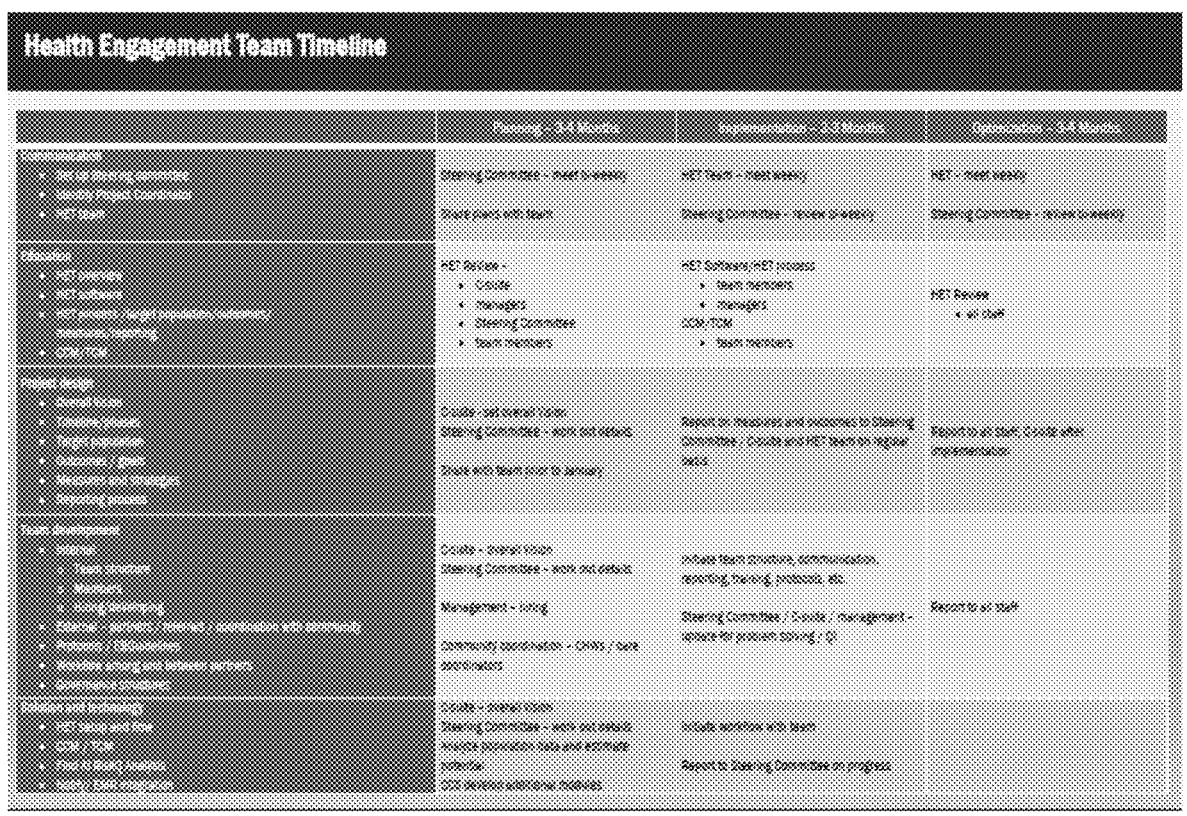
FIG. 41 is a chart illustrating the activities of the health engagement team over a period of time.
Figure 42:
FIG. 42 is an example of a health engagement dashboard.
Figure 43:
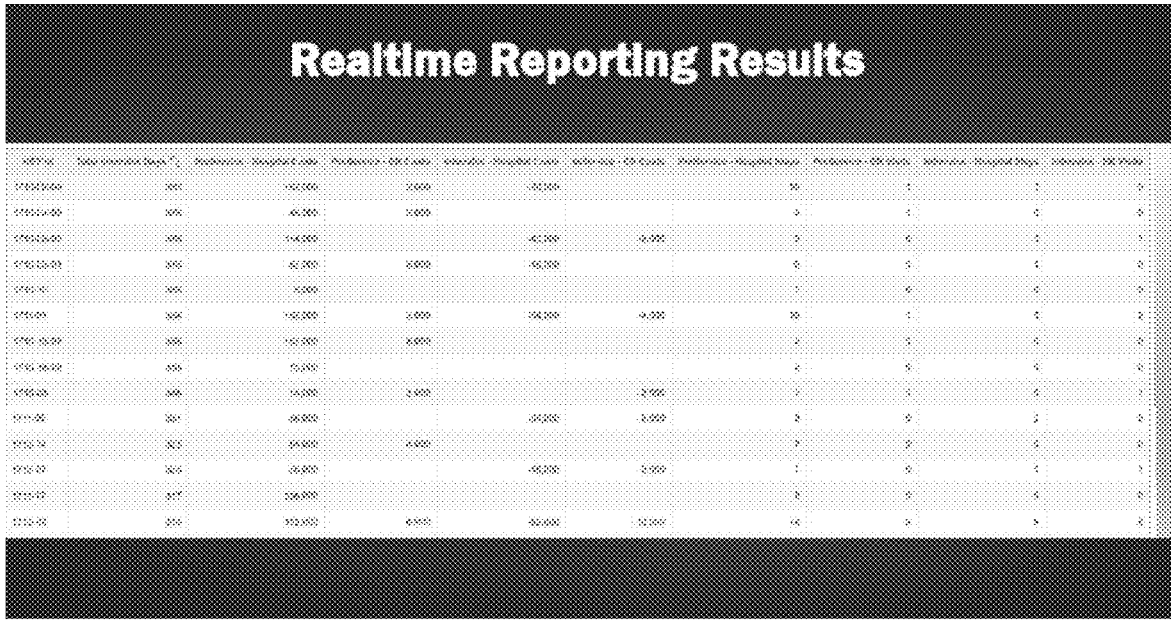
FIG. 43 is an example of the real-time reporting results provided by a Care Coordination System software application.
Figure 44:
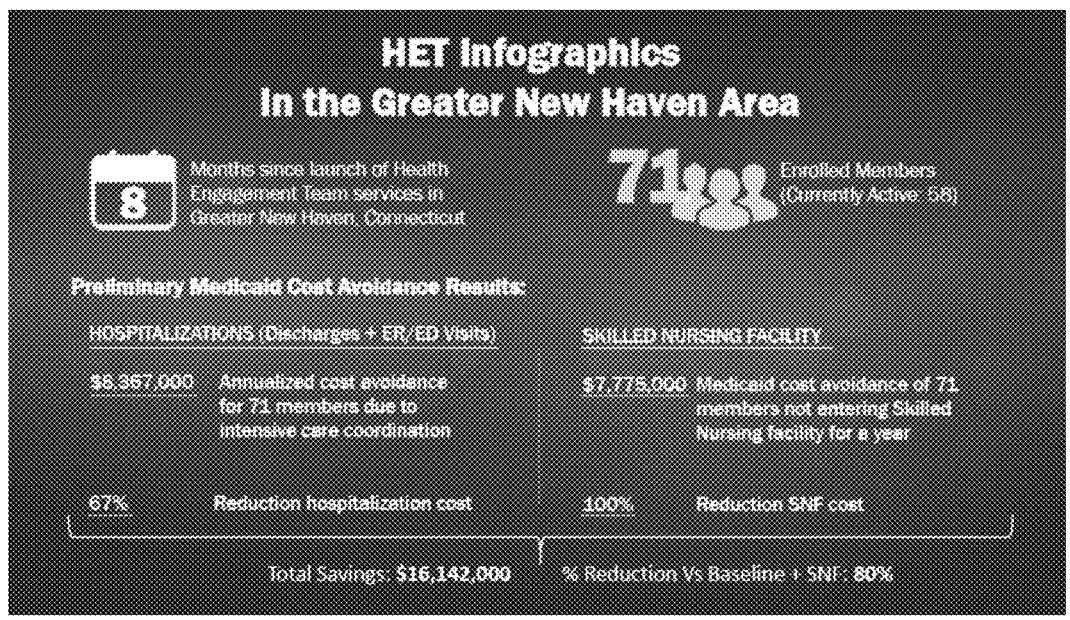
FIG. 44 is chart showing the financial benefits of implementing the Pathways Community HUB model within the Greater New Haven area.
Figure 45:
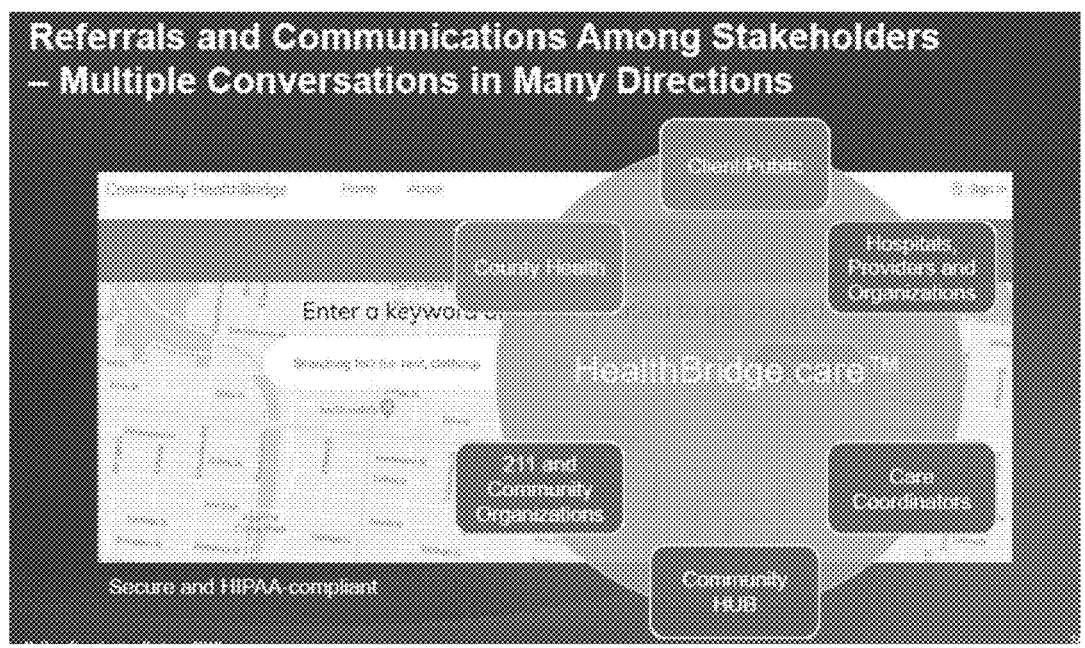
FIG. 45 is a diagram showing how the Care Coordination System software application acts as a central hub connecting Care Coordinators with patients and Care Coordinators and patients with various organizations.
Figure 46:
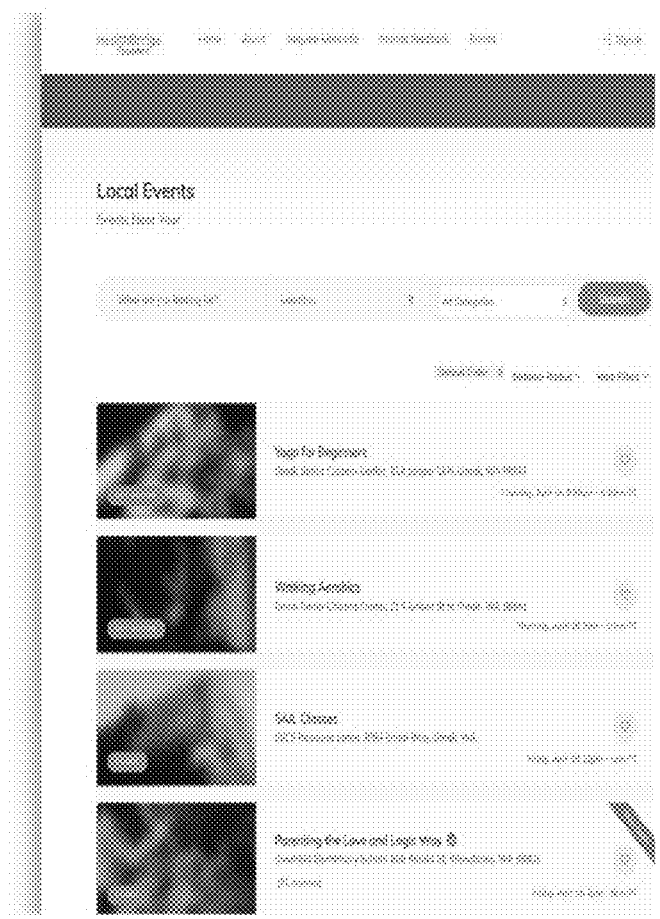
FIGS. 46-54 are screenshots of the Care Coordination System software application.
Figure 47:
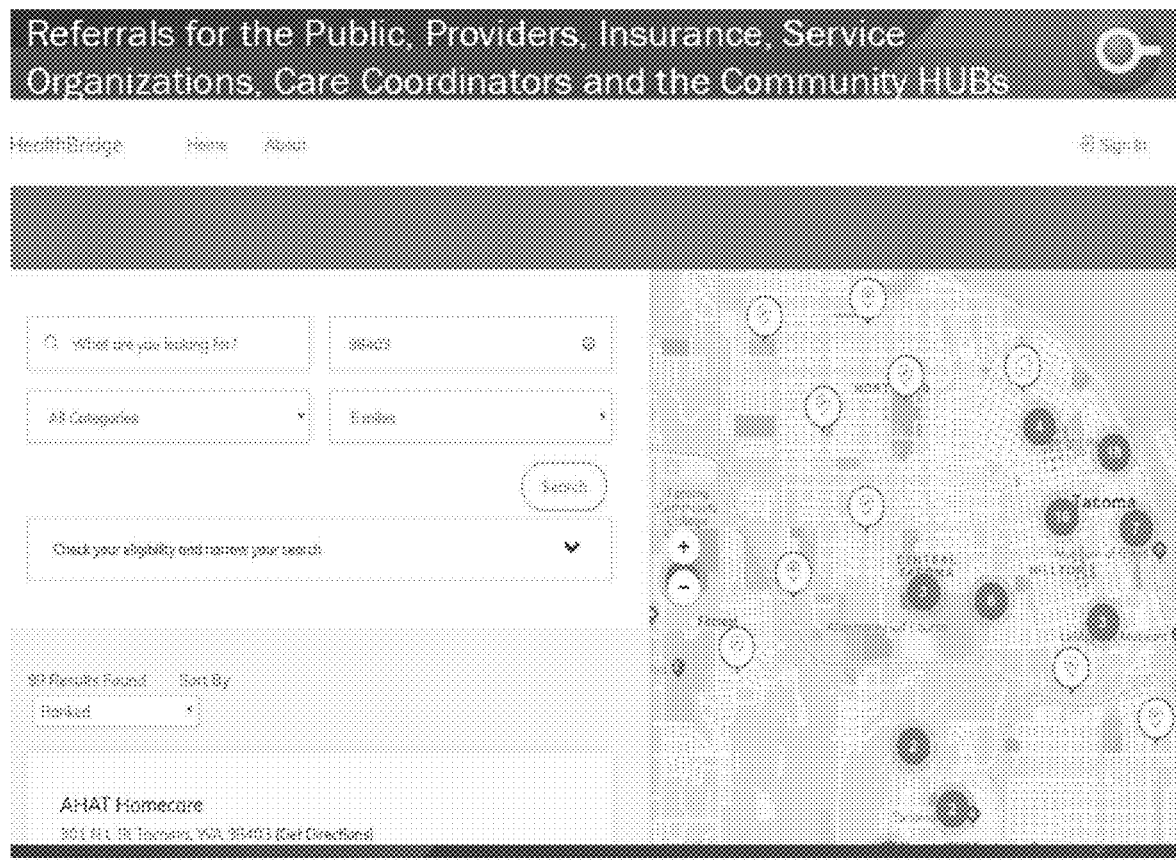
Figure 48:
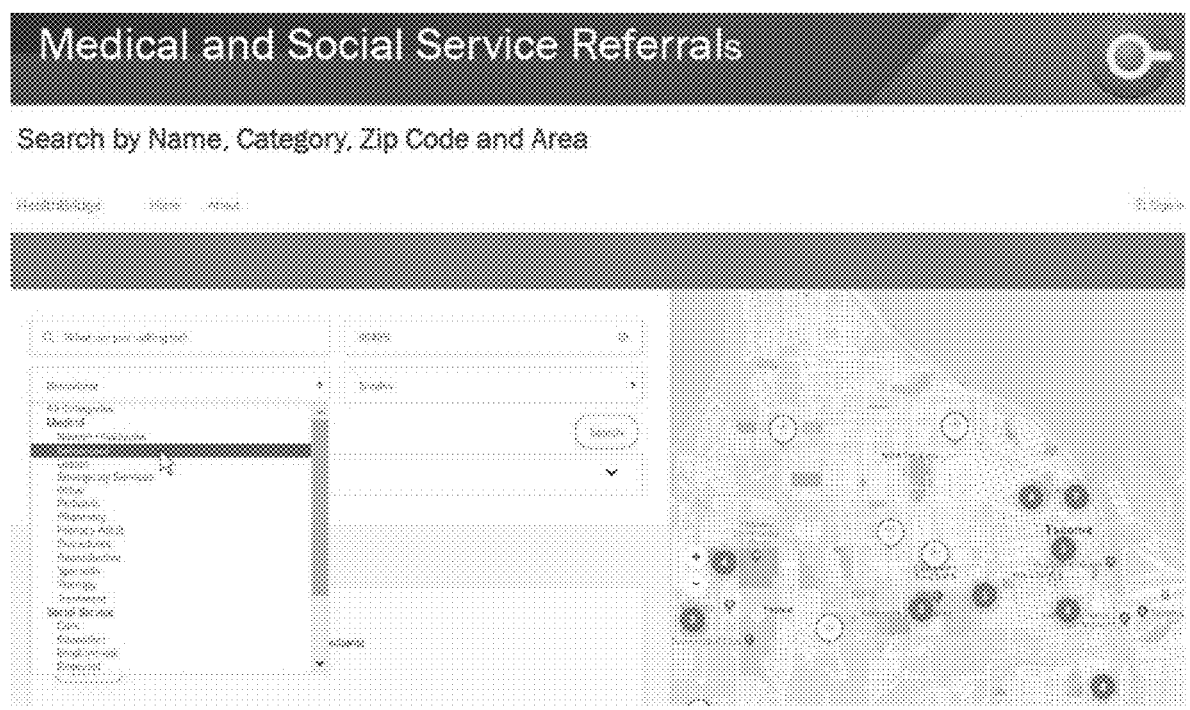
Figure 49:
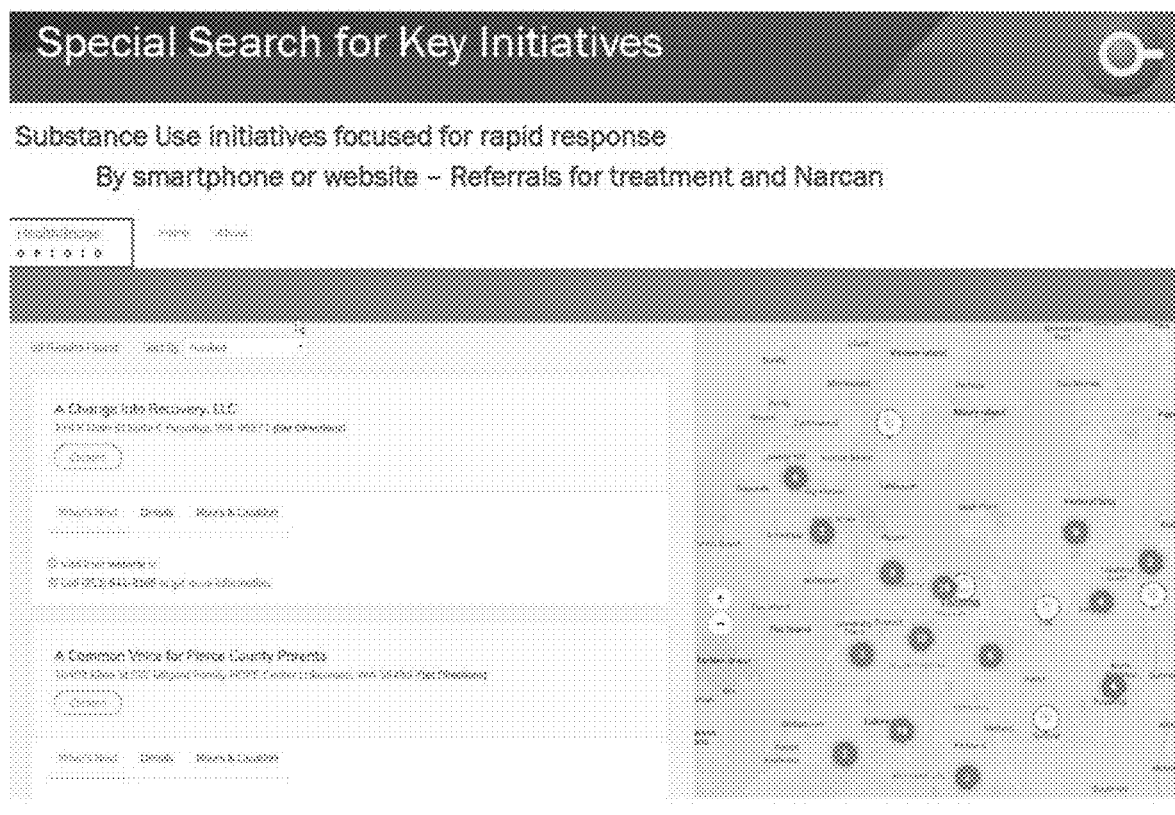
Figure 50:
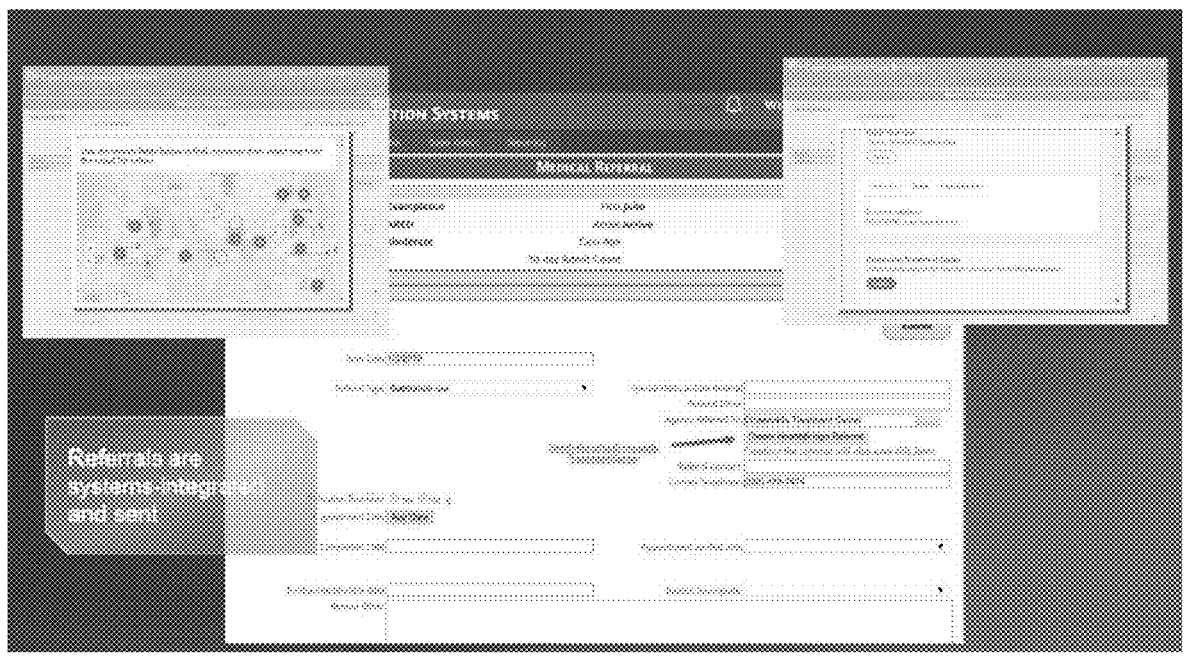
Figure 51:
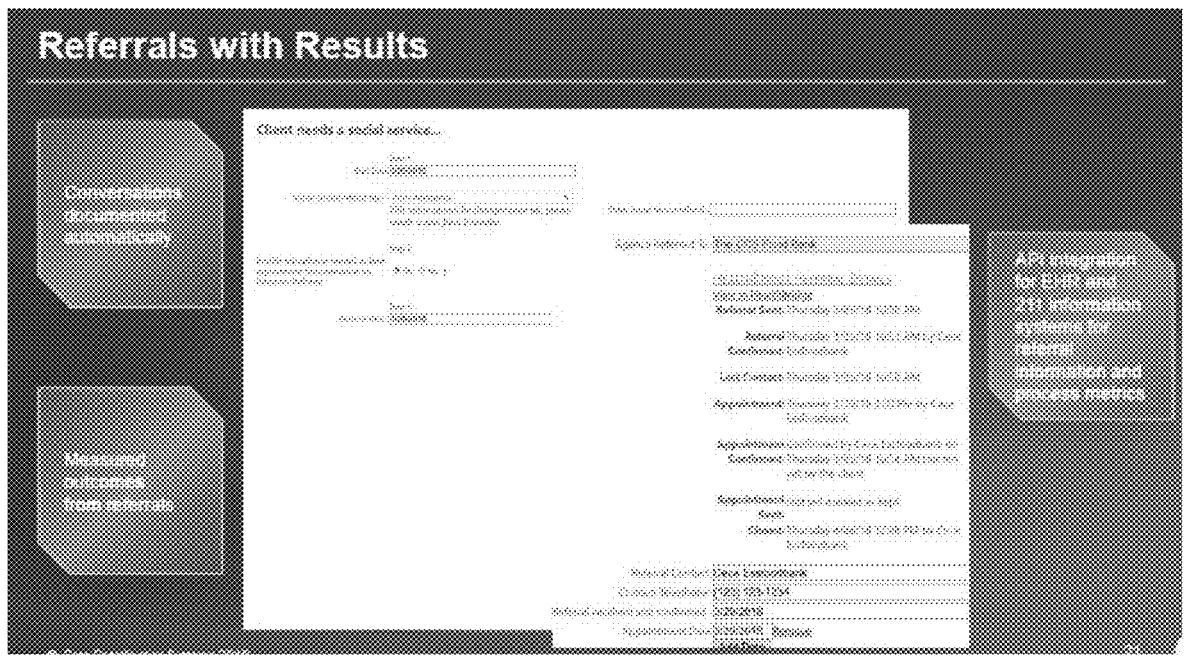
Figure 52:
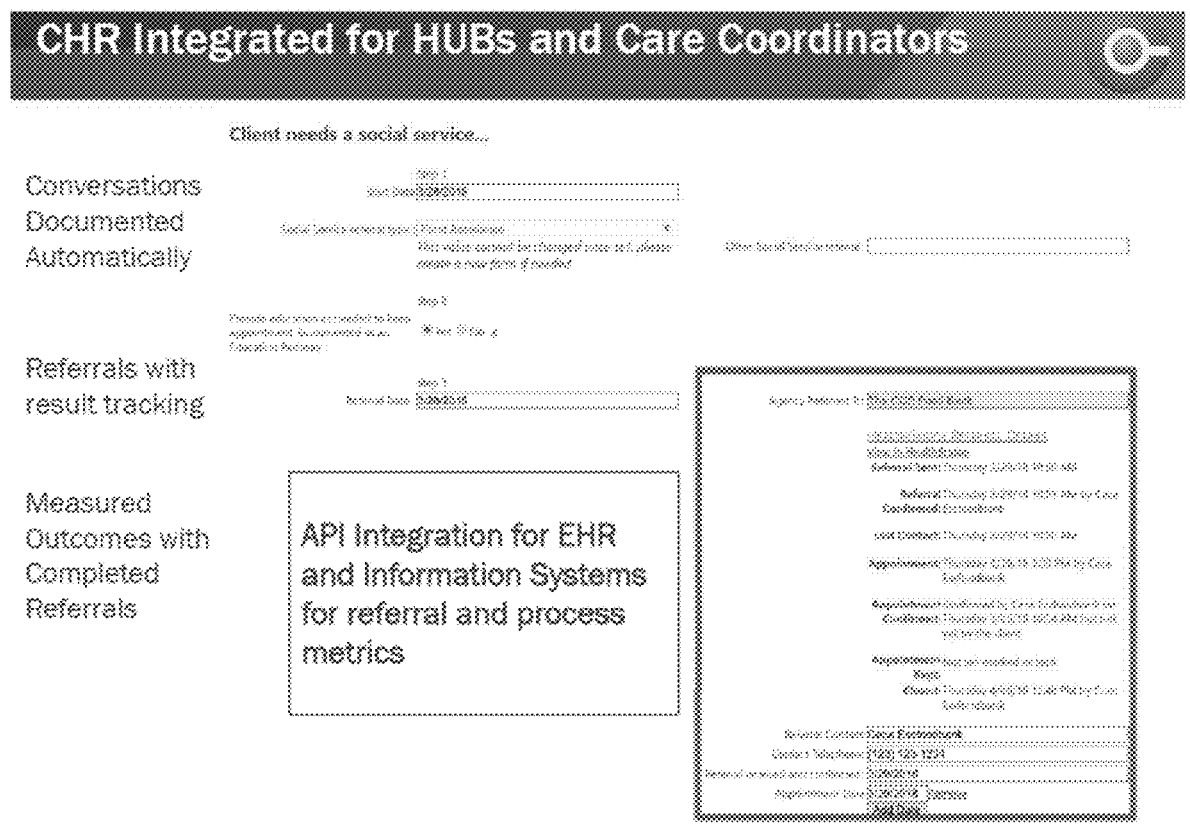
Figure 53:
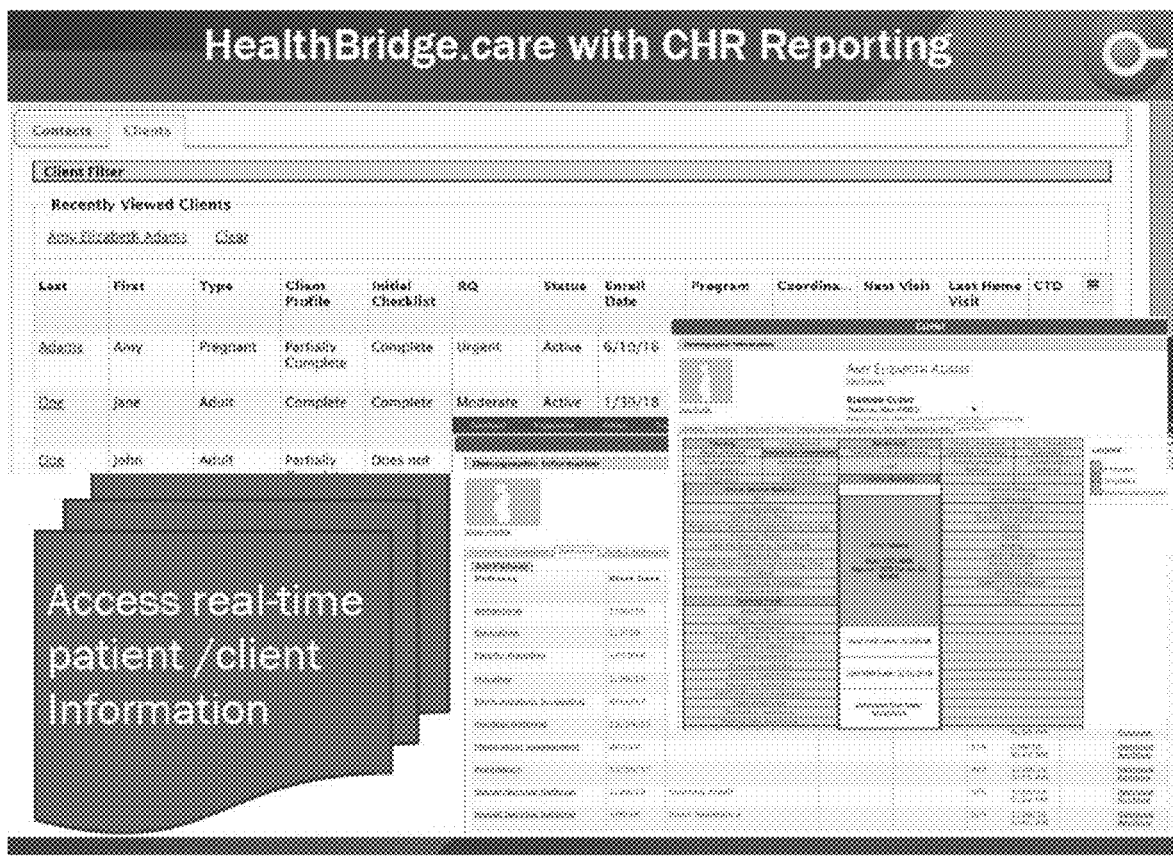
Figure 54:
Figure 55:
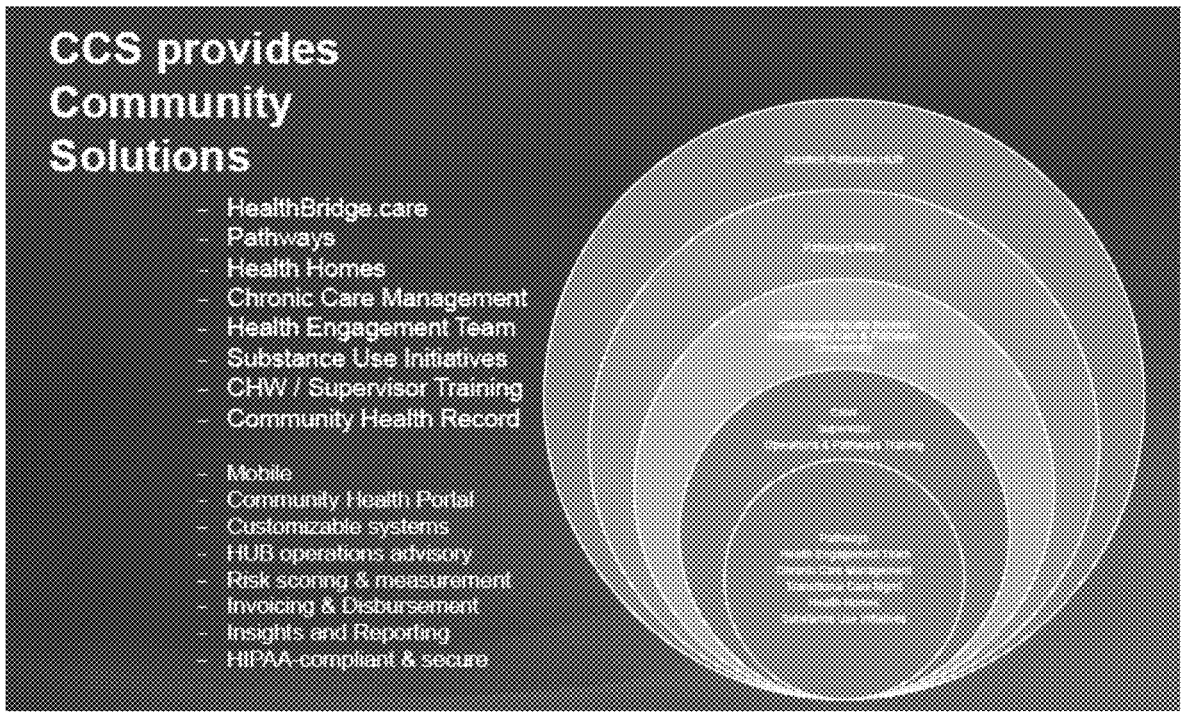
FIG. 55 is a chart showing the integration of component parts of the care coordination system.
Figure 56:
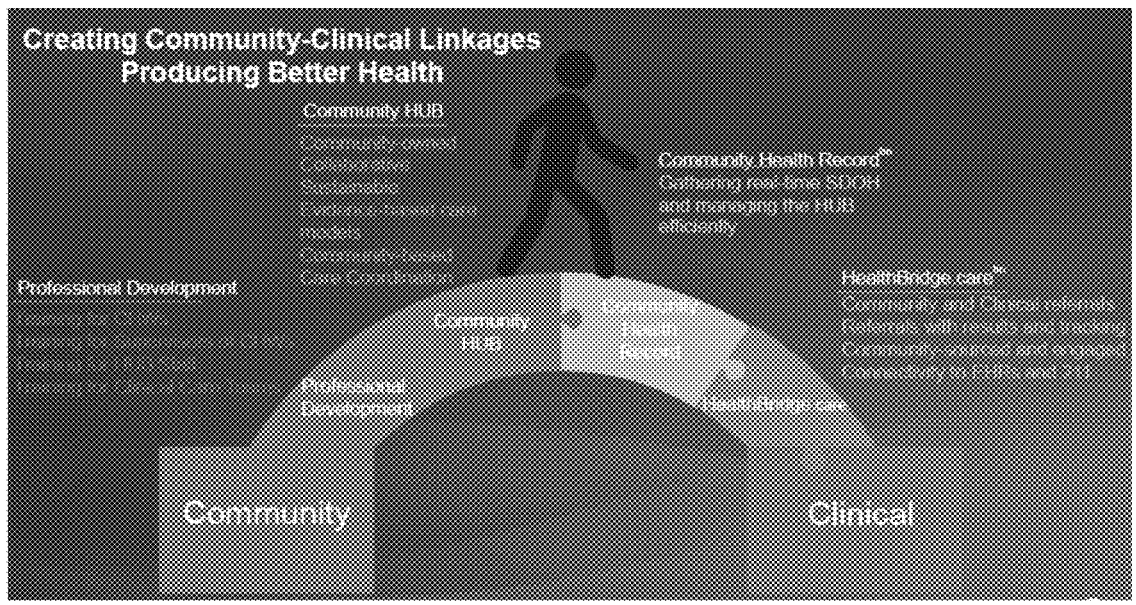
FIG. 56 is a bridge diagram showing how the community to clinical linkage is established.
Figure 57:
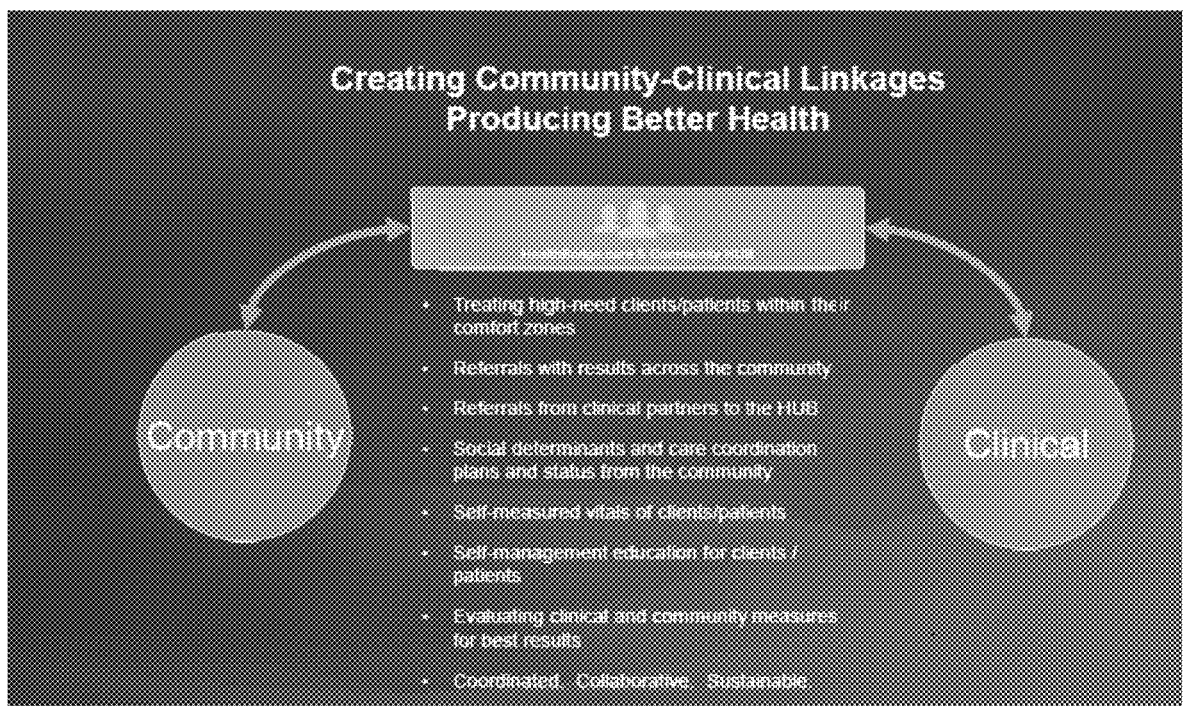
FIGS. 57 and 58 are diagrams which show features of the Care Coordination System software used to establish community to clinical and clinical to community linkages.
Figure 58:
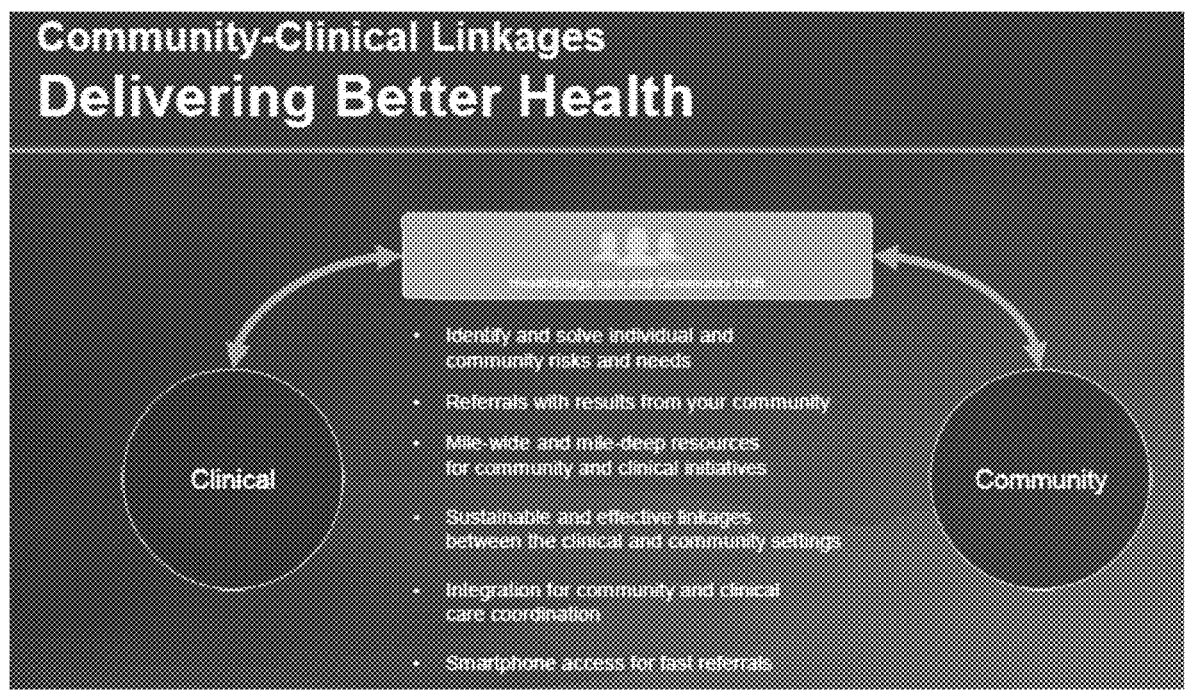

HUBs must first be certified by the national HUB institute before they may participate within the community. To receive HUB certification by the national HUB Institute, a HUB must use the standardized Pathways. A list of 20 approved Pathways, as well as a chart used with two of the Pathways, is found within FIGS. 4 to 24. Pathways are specifically designed to be clear and concise. New HUBs are not required to use all Pathways when they start up, however, they are expected to gain experience with the Pathways and to develop new Pathways when needed, with the support of the HUB Institute. By standardizing the Pathways, HUBs can compare outcomes across care coordinators, agencies, communities, regions, and States. Standardization also allows the development of universal billing codes to tie payment to outcomes. In Ohio, Medicaid managed care plans have developed contracts based on Pathway completion.

Many communities want to track more comprehensive measures, such as overall reductions in emergency department visits, improvements in hemoglobin A1c, and reductions in hospital readmissions. The HUB continues to track individual Pathways but can also "bundle" Pathways together to achieve a larger objective. For example, to reduce emergency department visits, most individuals may need to receive:

Ongoing primary care (Medical Home or Medical Referral Pathway);

Help with medication (Medication Assessment or Medication Management Pathway);

Education about their conditions, medication, or needed services (Education Pathway);

Help with housing (Housing Pathway); and

Help with barriers to connecting to other social services (Social Service Referral Pathway).

The Pathway bundle has a specific billing code, and funders can offer an incentive payment if all of the identified Pathways are successfully completed.

In some situations, some Pathways may not be completed, and the desired outcomes may not be reached for a given individual. In such cases, the Pathway still needs to be closed. The HUB record such cases as "finished incomplete." Pathway incompletion data is monitored by the HUB. The community care coordinator is required to document why the Pathway was not successfully completed. The HUB tracks which Pathways are not completed and compiles the reasons. For example, Pathways may not be completed because the resources are not available in a community. The community uses this data provided by the HUB to evaluate gaps in services and other issues that can be addressed on a policy level.

Pathways are the metric that focuses on successful resolution of an identified issue. Pathways are also the mechanism the HUB uses to tie financial accountability to completion. Completion of Pathways have demonstrated a significant improvement in patient outcomes and cost savings. The HUB provides the infrastructure communities need to support multiple and diverse agencies and related resources so they can work collaboratively to address health inequities and achieve real improvements for at-risk individuals.

Pathways Community HUBs may start in a variety of ways. Most HUBs have developed through the efforts of a small group of community-focused individuals determined to make a difference for their most at-risk citizens. For example, a HUB may start with the dedication of a few individuals such as community organizers, physicians and community leaders. HUBs are transformative by design, and it takes a determined core group of individuals with vision and dedication to make a HUB a reality. The HUB's primary focus starts with finding those most at risk in the community and ensuring that risk is reduced. This leads to better health outcomes and lower costs. The right community partners are engaged in the process to allow the appropriate connections to be established in building the network. A sense of community support and ownership lends ongoing support to the HUB. Most communities begin with a segment of the at-risk population, such as high-risk pregnant women, adults with multiple chronic conditions, or frequent users of hospital emergency departments. Once the infrastructure is in place, HUBs are designed to grow as the community gains experience with the model. Pathway funders are engaged at the very beginning of the community discussion about implementing a HUB. Health plans, hospitals, social service agencies, accountable care organizations (ACOs), foundations, and other identified "Pathway purchasers" are involved in defining the at-risk population and standard Pathways to be used. Care coordination agencies move from working in competitive silos to working as an unduplicated team with contracts and payments focused on outcomes in an accountable, business-focused model. Strong care coordination agencies that are effectively serving high-risk community members typically find that their reimbursement is increased with the HUB approach. Agencies that are not successfully engaging at-risk individuals or that do not follow up to connect them to services typically do not do well with this model. Payment is based on outcomes, and agencies must be able to confirm that risk factors have been effectively addressed. To achieve sustainability, the HUB develops and works toward expanding the number of funders supporting the HUB network. Agreements with the funders are designed to reflect the risk identification and risk reduction components of the HUB model. The HUB Institute has developed coding strategies for Pathways that can be used with multiple funders to achieve "braided funding."

Individuals at high risk for poor health outcomes have many different risk factors, and one funder usually cannot cover all the Pathways that need to be addressed. Identifying which funders will pay for specific Pathways is employed to develop braided funding and to adequately funding the community care coordinator. As community care coordinators in the field start to reach out and engage those at greatest risk, they begin the data collection process by completing the comprehensive assessment. As they use Pathways to address the risk factors identified by the assessment, the HUB provides an effective data flow and evaluation methodology to the community care coordinators that is easily accessible as well as simple operational reports for community care coordinators, supervisors, and administrators. These reports allow a quick view of how this "outcome production" process is proceeding at all levels: individual, community care coordinators caseload, agency, and across the entire HUB network. The reports are employed for the model to reach its maximum potential. The questions that reports answer include: "Are we reaching those at greatest risk?"; "What risk factors are being identified within the population we are serving?"; "How much time does it take to address these risk factors?"; "Which care coordinators and which agencies are able to address the risk factors the fastest?"; "What strategies are the most efficient care coordinators and agencies using to quickly address the risk factors?"; and "What risk factors are taking the longest to address or cannot be addressed, and what are the reasons?" Obtaining effective technical support and carefully understanding the evidence-based standards and principles of the HUB model are components of effective HUBs. The HUB Institute provides technical assistance in key areas of model implementation, especially in support of the national standards. The original Community Care Coordination Learning Network (CCCLN), supported by the Agency for Healthcare Research and Quality (AHRQ), provides the foundation for the development of the national certification process. There are also vendors available to provide operational support to HUBs with regard to implementation, training, technology, and contracting for care coordination services. Newly developed and existing HUBs are designed to focus on and work toward national HUB certification. When the CCCLN evaluated HUBs that developed over the past 10 years, it found that as many as one-third were not successful or sustainable. HUBs that did not seek specific technical support for the model and did not focus on the evidence-based standards were unable to demonstrate outcomes. It is very difficult to make a case to funders to support the HUB infrastructure without demonstrating improved outcomes and reduced costs. HUBs that focus on the national standards and enroll in certification demonstrate significantly better outcomes and sustainability.

HUB directors, public health leaders, third party payers, policymakers, and other community stakeholders have requested certification of the HUB model. This certification provides standards and expectations for HUB implementers and payers. The HUB Institute—with funding from the Kresge Foundation and in partnership with the Community Health Access Project, Communities Joined in Action, Georgia Health Policy Center, and Rockville Institute—is leading the HUB certification process. Certification supports current and future HUBs by requiring (1) the evidence-based and best practice components known to be essential for high-quality community care coordination services and (2) an efficient regional infrastructure that can lead to improved health outcomes and reduced costs. The standards support a basic framework of quality that encourages local variation and innovation within various cultural and geographic settings. Certification enables funders and policymakers to make wise investments in care coordination services that ensure quality, health improvement, and the value of contracted services. The complete prerequisites and standards for HUB certification can be found at the HUB Institute Web page. This section highlights some of the key elements that are required.

By definition, the HUB is a neutral and independent legal entity that has legal capacity to enter into agreements or contracts. Many of the certification prerequisites and standards tie directly into the governance of the HUB, including the following items.

Governance Documents

1. The HUB coordinates a network of care coordination agencies serving at-risk clients. The HUB has legal documents describing the relationship between the HUB and care coordination agency members. The HUB model is designed to use what is already working in communities, including existing care coordinators and agencies. Most communities have funding in place for a variety of care coordination work, but the infrastructure for creating a network of agencies together is lacking.
2. The HUB has contracts with a minimum of two payers to ensure comprehensive and sustainable care coordination services. Contracts confirm that a minimum of 50 percent of all payments are related to an individual's intermediate and final outcomes/Pathway steps.
3. The HUB documents that it complies with the Health Information Privacy and Accountability Act through training, policies, and signed agreements.
4. The HUB operates in a transparent and accountable manner and has policies around conflict of interest and distribution of referrals to care coordination agency members. It is a requirement that the HUB not directly provide care coordination services.

Needs Assessment

The HUB reviews and/or conducts community needs assessments. This assessment should include local data specific to medical, behavioral health, social, environmental, and educational factors and guide the HUB in its efforts to improve health and reduce inequities. The HUB needs to show how it uses the community needs assessment to identify the populations to be targeted for community care coordination services.

Care Coordination Program Requirements

The HUB creates agreements with each care coordination agency to delineate expectations around hiring, training, and supervision of CCCs. In addition, the administrative staff of the community agencies need training and support to become part of a network of agencies focused on finding those most at risk and connecting them to care. Experienced, capable, and creative HUB leadership is needed to help agencies move away from being competitive silos and make the transition toward functioning as a team.

The HUB is responsible for monitoring the performance of its care coordination agency members and for improving the quality of care coordination services. Written agreements are required to ensure clarity and transparency of the roles of the HUB and care coordination agency members and the financial arrangements between them.

Many of the HUB standards define policies and expectations for participating programs, agencies, and providers or for community care coordination services. It is required that the HUB have operational policies and procedures in place that cover client enrollment, allocation and monitoring of referrals, documentation requirements, ratios of CCCs to clients, and other key operational items.

Data Collection and Payment System Linked to Outcomes Pathways

The HUB is required to use standardized Pathways approved by the HUB Institute. Pathways are to be used as defined, and new Pathways cannot be developed without submission to the HUB Institute for review. Pathways outline key stages required for the delivery of high-quality and efficient care coordination services. Each Pathway focuses on one significant client need or problem and identifies and documents the key steps that lead to a desired, measurable outcome. In addition, standardized Pathways allow research, evaluation, and best practices using standard metrics.

The 20 standardized Pathways link billing codes to Pathway steps. Payment for outcomes is a key component of the HUB model and promotes accountability, quality, equity, health improvement, and value. Contracts with payers must specify that at least 50 percent of all payments are related to an individual's intermediate and final Pathway steps. Prior to the launch of HUB operations, a tracking and payment system must be developed that rewards participating organizations and individuals based on the completion of Pathways. Participating agencies within a HUB must be rewarded and incentivized to work in collaboration with other agencies to reach those at greatest risk and connect them to care, recognizing that those individuals require more time and expertise to serve.

Client Information

The HUB collects client demographics and other relevant information to effectively address the medical, behavioral health, social, environmental, and educational needs of the at-risk client. FIG. 25 is an example of a demographic intake form, which is used to obtain key information about the client upon enrollment in the HUB. Checklists capture specific information about the client's health and social issues at each face-to-face encounter. The checklists should document any identified risk factors and provide information for the initiation of Pathways. A more comprehensive checklist is used at the initial visit, and shorter checklists are used on an ongoing basis to monitor changes between visits. FIG. 26 is an example of a checklist used for adult clients. Other client information can be gathered through standard tools or screens, such as the Patient Health Questionnaire (PHQ), a depression screener; Ages & Stages Questionnaire (ASQ); and Patient Activation Measure (PAM).

Risk Assessment

To ensure an at-risk individual's needs are being addressed and met- and an efficient use of limited resources—the HUB assesses and monitors each client's risk factors. The HUB describes how risk measurement translates into intensity of care coordination services.

Data System

The HUB tracks, monitors, and reports on client services and promotes collaboration, intersectoral teamwork, and community-clinical linkages. Although a complex data system is not mandatory, the HUB develops accurate and efficient methods for tracking and monitoring data collection for at-risk clients. Most HUBs will rely on information technology to perform this task. Whatever approach is used, this system ensures the protection of client information at all times. The HUB ensures that clients (1) are identified and engaged; (2) are evaluated to determine their needs, risk factors, and risk level; (3) have an individualized care plan; (4) are assigned to appropriate standardized Pathways; (5) are monitored through the completion of the appropriate Pathways; (6) receive home visits; (7) are reevaluated to determine needs, risk level, and service adjustments; and (8) are discharged when their needs are met. Communication and data sharing among practitioners, agencies, community care coordinators, and the client help ensure quality and continuity of services.

Quality Assurance

The HUB is responsible for monitoring and improving the quality of care coordination services provided to those who are at risk. Therefore, the HUB has a quality improvement plan and regularly evaluates its services as well as those services provided by care coordination agency members. The HUB quality improvement plan should describe how quality improvement projects are selected, managed, and monitored. The HUB implements a communication strategy that covers planned quality improvement activities and processes and how updates will be communicated regularly to all involved.

The HUB is to also monitor the performance of its care coordination agency members and offer technical assistance to ensure quality and client safety.

Community Care Coordinator Requirements and Training

Many different types of professionals can serve as community care coordinators, including but not limited to social workers, community health workers, nurses, and case managers. By definition, these individuals spend the majority of their time meeting face-to-face with clients in a community setting, including the home. To ensure the provision of high-quality services and effective collaboration across all providers, each HUB develops basic human resource requirements for care coordinators, along with a comprehensive training program. Individuals receiving care coordination services are often dealing with complex health and social issues, and community care coordinators need adequate preparation. The HUB employs clear policies and procedures on all aspects of training, documentation, and accountability for results.

The HUB model of care coordination focuses on improving health, advancing equity, improving quality, and eliminating disparities, and all HUB and care coordination agency personnel complete cultural competency training.

Community care coordinators are supported and supervised by a competent professional, working within the scope of his or her license. The level of supervision varies based on the training of the community care coordinator. It is required that community health workers have supervisors who review and sign off on documentation.

Education, training, and support for community health workers and for community care coordinators other than community health workers are employed to achieve improved outcomes for those clients at risk. The HUB provides documentation that community care coordinators meet the minimum training requirements required as part of certification.

For example, Community Care Coordination training may consist often days of classroom instruction and group activities to build competency in health knowledge, care coordination, relational skills, coaching skills, community outreach, and basic organizational skills, with integrated software training. Training may also consist of online E-Lessons which covers the human life span with a focus on physical, cognitive, mental & social development from a Community Health Worker perspective. Additional training may be provided in the form of a community-based practicum consisting of a minimum of 130 hours over 6 weeks in the field at the trainee's agency to enhance care coordination experience. Training of supervisors of Community Health Workers and Community Care Coordinators may consist of dynamic interactive and experiential training wherein a coat-team approach is utilized for achieving successful coordination and productive care coordinators.

Health Engagement Team

The Pathways Community Hub model also provides the opportunity to implement a health engagement team. A health engagement team is a combination of multi-disciplinary professionals and community health workers which typically includes a primary care physician, nurse practitioner, mater social worker, behavioral health specialist, pharmacist and community social workers. The health engagement team may be specifically tailored or customized to the patient. Oftentimes, a health engagement team is employed to help manage a client's long standing and high cost health conditions. Health engagement teams also assist in transitioning the patient to a high touch, long-term relationship community-based care coordination when appropriate.

The community care coordination process typically begins with the health engagement team engaging with the patient in the hospital setting. After the patient is released from the hospital, members of the health engagement team may meet with the patient at his or her home or other comfort setting. The health engagement team establishes a team assessment of the patient's condition and develops a protocol for primary and behavioral care.

There are numerous advantages to implementing a health engagement team. These advantages include the following: reduced emergency room visits and emergency department utilization, reduced admissions to skilled nursing facilities by diverting care, improving chronic disease management with evidence-based clinical guidelines, improved medication adherence, reduced ambulance transits, reduced 911 and EMS calls, reduced isolation through high visit frequency by health engagement team members, reduced healthcare costs, improved patient health. The benefits of employing a health engagement team are indispensable. For the accountable care organization, the health engagement team provides increased provider engagement, substantial new revenues, reduction in non-primary controllable costs, improved health benefit ratio, significant shared savings and gains, efficient outsourcing to health engagement team services from providers and the establishment of clinical-community linkages. A health engagement team may be instituted as a component part of the Pathways Community HUB model and as discussed in greater detail below, may provide numerous interested parties or service providers involved with utilizing the community care system software application disclosed herein.

Summary of HUB Model

The identification and strategic reduction of an individual's risk factors represent an opportunity to address disparities and reduce costs. The Pathways Community HUB model builds the community infrastructure and provides the tools, standards, and strategies to implement this approach for individuals and populations. Across the Nation, there are effective and capable community organizers, with support, they can use existing resources to implement this HUB model and bring about transformative change.

Software Application

As used in this application, the terms "component", "module", "system", "interface", or the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. The term "client" referred to below, refers to any individual accessing and using the computerized method and system or software application.

Provided is a computerized method and system for coordinating medical care, health treatments, social services and other types of services between patients, care coordination agencies, community care coordinators through a Pathways Community Hub. The system comprises one or more client devices and a server computer. The client device may be any type of computerized device capable of executing instructions stored on the client device. The client device may be a laptop computer, desktop computer, tablet computer, or wireless cellular device. The server computer is communicatively coupled to a plurality of client devices. The server computer may be directly linked to the client devices or communicatively coupled through a network connection, like the internet. The system may have one or more software modules stored on the server computer and client device. The software may be fully executed on the server computer while the client interacts with the software module from the client device through a network connection. Alternatively, certain software modules may be stored and executed on the server computer while other software modules are stored and executed on the client device. In the preferred embodiment, each client utilizing the system, including patients, care coordination agencies, community care coordinators, creates a unique user ID and password for accessing information.

The computerized method and system may be in the form of a web-based software application referred to as a Care Coordination System (CCS). The web-based software application allows clients or patients to log-in to the system and to seek various types of medical services, health services, social services or other types of services. The application operates by allowing a patient to enter a query within a search engine integrated within the CCS or software application to search for the types of medical, health or social services desired. After entering the query and submitting the search, the CCS or software application returns a number of hits which include facilities or service providers who are capable of fulfilling the patient's request for services. The information provided to the patient in response to the patient's query includes information about each service provider including but not limited to information concerning the service provider's location and hours of operation. After finding the desired service provider, the patient can send the service provider a message through the CCS software application requesting an appointment to obtain the medical, health or social service desired. The patient's request or referral is received by a community-based organization (CBO) member who manages the community-based organization's patient referrals. In certain instances, the CBO member receives an email alert (or any other type of electronic alert within the purview of a person of ordinary skill in the art) containing the patient's referral. The CBO member may then confirm receipt of the referral through the CCS software application, for example, by clicking a confirmation button. The patient and CBO member can view the following information on the display page of the CCS software application: the service provider, contact date, referral request, referral confirmation, appointment date, appointment confirmation and messaging screen. Communication between the CBO member and the patient may occur directly within the messaging screen within the software application. This allows for the creation of and confirmation of an appointment directly within the software application.

The computerized method, system and web-based software application also includes a Care Coordination System (CCS) hub portal. The CCS hub portal is managed by a hub portal user. The CCS hub portal includes a listing of clients or patients, including client information and referral information. Community resource listings are uploaded by the HUB user and maintained by agencies through agency logins where they also track and respond to referrals. The CCS hub portal user can enter a patient's account for the referral and view the entered information. The CCS hub portal user can also monitor the communication between the patient and the CBO member, Community Health Worker (CHW), community care coordinator or service provider to make sure that everything is running smoothly and that the patient is obtaining the help he or she needs. Once the appointment is kept, the service provider may send a message through the messaging screen on the CCS software application to the patient to conclude the service. This will cause the CCS hub user to close the referral. The referral is then closed for the sake of tracking. The CCS hub user may then move or archive the referral to the historic tab and be complete the task without any further interaction from the service provider, community care coordinator or community health worker.

The computerized method, system and web-based software application may include a health bridge referral component. To create a health bridge referral from within the CCS hub portal, the CCS hub portal user first enters the patient's account to access the patient's client view. The CCS hub portal user may be any interested party including but not limited to a member of a health engagement team, a hospital, physician, health care provider, a community care coordinator, a community health worker, a community-based organization or agency, etc. The CCS hub portal user then adds the type of referral requested (e.g., medical referral, social service referral, health referral, etc.) conducts a search through the search engine of the CCS software application and selects a service provider, community care coordinator, community health worker and/or community-based organization to treat the patient. Fields related to the referral are then populated with information concerning the service request (e.g., the service provider, appointment date, location, time of appointment, etc.). This information is then populated within the referral form. The referral may then be made through an input button on the CSS software application. The service provider, community care coordinator or community health worker representative receives a communication (e.g., an email, text, etc.) to notify the selected service provider, community care coordinator or community health worker of the referral. The service provider, community care coordinator or community health worker representative then enters the CCS software application and confirms receipt of the referral. The service provider, community care coordinator or community health worker representative then sets an appointment date and sends a message through the message screen on the CCS application directly to the patient. The service provider, community care coordinator or community health worker representative can then confirm the appointment within the CCS hub portal by clicking an input button to transmit a notification to the patient on the CCS software application that the appointment has been confirmed. The CCS hub portal user can confirm that the appointment is kept within the CCS hub portal and send a message to the patient community care coordinator, community health worker or community-based organization. The CCS hub portal user may enter the hub portal, view the entire conversation between the patient and the service provider, community care coordinator or community health worker representative, view that the appointment was kept and view all of the information that was automatically entered within the CCS hub portal. The patient may also enter the CCS hub portal and view the conversation, the appointment details and enter comments about the services provided. Through this process, the patient, the service provider, community care coordinator or community health worker representative, the community-based organization, the client, etc. is kept up to date with clear concise tracking of the services provided. HealthBridge is an information referral platform integrated with the Pathways HUB Connect platform (CHR) as a standard feature providing security of information, reporting, auto-generation of pathways for HUB clients, and integrated resources for care coordinators to select and send referrals to agencies. The public-facing website and public integration with the HUB is the stand-alone and an optional integrated feature. Healthbridge may be used to partner with 211 systems, add other directories, and engage with community organizations for better health. Healthbridge is smart-phone and text enabled and connects with HER systems and provides patient referral results. It is integrated with the Community Health Record for community-based care coordination and sustainability and provides real-time information for all stakeholders.

In certain embodiments, the computerized method, system and web-based software application functions as a community resource and referral source offering a secure portal for public and HUB client use. The computerized method, system and web-based software application facilitates and tracks multi-directional conversations/referrals between a client, the care coordinator and community-based organizations (and care coordinators). A public-facing website is provided which is a stand-alone application that exceeds the capabilities of other information and referral (I&R) services not only in that it provides a much more interactive platform between patients and service providers but it also takes an active approach in processing patient data for invoicing, future referrals and tracking successful completion of pathways for patient satisfaction, future pathway referral recommendations as well as for billing purposes. Additionally, when a Pathways HUB is also involved, the public-facing website integrates with the HUB to benefit community members, HUB clients, care coordinators, community service organizations, hospitals, providers, and managed care organizations.

Public and HUB clients may seek local referral sources through a search engine within the web-based software application and send requests to third party agencies or community-based organizations or to community care coordinators or community health workers. Public and HUB clients may maintain secure user logins for their referrals and communications with such third-party agencies. These agencies are notified via email when a referral is made to them.

The computerized method, system and web-based software application may include a scheduling component. As described above, the scheduling component allows for appointments to be created between the patient and the service provider, community care coordinator or community health worker.

The computerized method, system and web-based software application may include an appointment feedback component. The appointment feedback component provides notice to the party referring the patient for an appointment with a service provider that an appointment has been kept. The appointment feedback component may transmit such notice to the referring party electronically, for example, via email, text message or any other means within the purview of a person of ordinary skill in the art. HUB clients have added benefit as their community care coordinator is also receiving the referral information.

The computerized method, system and web-based software application may include a health record integration component which allows physicians, health care providers, hospitals, clinics, etc. to merge an individual's "electronic health record" with a health care organization (e.g., a hospital, clinic, physician's office, etc.) with a "community health record" established through use of the CCS software application. The health record integration component may be established through an input button on the CCS software application which may be clicked by the physician, physician assistant, health care provider, etc. to upload a patient's electronic medical records onto a patient's account on the CCS software application. This allows both patients and users of the CCS software application to view both a patient's electronic medical records and community health records entered into the system through appointments made through the CCS software application.

The computerized method, system and web-based software application may include a messaging component. The messaging component may allow for multi-user, real-time communications between the patient and the service provider such as a community care coordinator, community health worker, community-based organization, physician, hospital, etc. In certain embodiments, the computerized method, system and web-based software application may include a direct messaging component.

The computerized method, system and web-based software application may include a monitoring component. As described above, the monitoring component may allow health care providers such as physicians, health workers, clinics, hospitals, etc. to monitor communications between the patient and the service provider, community care coordinator or community health worker within the CCS software application including communications made via email, communications made within the messaging component of the CCS software application and any other communications made through the CCS software application. The monitoring component will also allow health care providers to monitor a patient's community health records entered into a patient's account within the CCS software application.

The direct messaging component allows the patient to communicate with the service provider, community care coordinator, community health worker, community-based organization, physician, hospital, etc. confidentially in a secure environment. Communications sent through the direct messaging component are not recorded within the patient's file or community health record and are not viewable by third parties.

The computerized method, system and web-based software application may include a tracking component. Information is entered into the system or software application from completed Pathway forms. Thus, pathways track the outcomes as agencies community-based organizations perform.

The computerized method, system and web-based software application may include an archiving component. The archiving component allows for recording and storing of patient community health records related to service visits, general patient records, general data entry related to the specific services provided, etc.

The computerized method, system and web-based software application may include an auto-invoicing component. The auto-invoicing component may work in conjunction with the archiving component to automatically generate bills for the services provided to the patient.

The computerized method, system and web-based software application, may also measure, display and process data related to the care delivery process. For example, upon entry of data related to a patient's community health record, the CCS software application may run processes analyzing such data and output recommendations further pathway referrals. The CCS software application may also run processes analyzing multiple patient data within a particular region and output data directed health related trends within a particular region and provide pathway recommendations for individuals having similarly situated health issues within a particular region.

The computerized method, system and web-based software application provided above allows HUB clients to use their own community care coordinators to receive referrals.

The computerized method, system and web-based software application also includes a referral resource ranking component. Community care coordinators, community health workers and other service providers are provided a curated list of referral resources that are ranked according to performance, as well as, curated and maintained by HUB operations. This provides for rapid response and modifications to the community resources listings and better referral resources for the community care coordinator, community health worker, service providers and community members.

The computerized method, system and web-based software application provides a secure web portal for clients and family members providing access to community resources, health decision support, appointments and communication with their care team. Health risk assessments (HRAs) are completed annually by the clients or patients and linked with the care team and Pathways Community HUB. Deeper medical knowledge is available to the client or patient through the health decision support and e-learning. Social information, clinical information, care plans and care team converge to assist the client with Pathways Community educational and engagement resources and action tracking tools.

The computerized method, system and web-based software application also includes options for an online and paper-based or larger health risk assessments designed specifically for Medicaid plan members (newborns through adult allowing for individuals with guardians and IDDs) for priority-driven targeted outreach and care management.

Health risk assessments can be completed via an online portal, through paper questionnaires (mailed or emailed), and/or by health plan staff during phone calls to/from plan members and/or visits to home. Health risk assessments and online portal may be branded with additional customization options—e.g., questions, reports, risk-logic, content, rewards-action tracking functions, SSO and other links. The online portal may also include e-lessons, videos, and decision tools for elective procedures and other topics. Content, tools and functions vary by member, administrative and clinical login. Health risk assessments and the online portal are HIPAA, ADA, GINA and FCC compliant.

The computerized method, system and web-based software application also integrates community resources with Pathways referrals and measurements. This allow the HUB and its community-based care coordination to be linked with other non-HUB community service organizations. The community care coordinator, community health worker or service provider determines which organization should be contacted to help the client or patient with their needs. The community service organization receives a secure referral and emails from the platform that they acknowledge. Communication and appointment tracking occur with the entry of Pathways within the web-based software application.

In certain embodiments, the computerized method, system and web-based software application provides the following additional features:

- The ability to have two, three, four, or more documented bi-directional conversations regarding a referral in the field of care coordination;
- The ability to have conversations via smartphone, text, tablet, desktop or any web browser enabled device;
- The ability to record/document conversations in a database, displayed in structured documents which may be transmitted via API or direct messaging to be consumed by other systems and/or posted to client/patient records;
- Metrics related to the conversations are recorded/documented in a database, displayed in structured documents, and may be transmitted via API or direct messaging to be consumed by other systems and/or posted to client/patient records. These values include but are not limited to, IP address of referral, referral date/time, referral type, referral category, referral eligibility requirements selected, confirmation date/time by recipient, acknowledgement by sender, appointment created (logical), time to create an appointment, appointment date set, appointment date/time/place, appoint kept (logical), appoint kept date/time, appoint kept with notes, follow up required;
- The ability for all stakeholders to review conversations and date/times;
- The ability for administrators to designated resources as favorites;
- Favorites are positioned in lists at the top
- Metrics are scored and ranking of scores of resources are placed in the lists based on the best rankings at the top for the specified search category or search criteria;
- Reporting on referrals which is made available for all stakeholders based on their role in the referral process;
- Multiple administrators are available to add, delete, deactivate, modify, curate resources;
- Any geo-location resource or information may be displayed and available via multiple metadata search tags;
- Special splash pages based on search criteria or category may be generated by the system for further engagement with the client;
- Marketing sponsorship pages and positions in lists may be made available;
- Payments due to resources are determined by rankings, results, surveys, favorites and performance;
- Administrators may designate which resources are involved in payments;
- Sponsorships may enter into contracts for referrals or views;
- Integrated with the Community Heath Record (CHR) platform to enable usage of the resources administered with the CHR;
- Given a client/patient is a member in the CHR, the referral will auto-generate a structured care coordination document for stakeholders in the CHR domain;

A client/patient's health and social needs/risks can be used by the CHR using artificial intelligence (AI)/machine learning to suggest possible recommended referrals;

A client/patient's health and social needs/risks can be used by the CHR using artificial intelligence (AI)/machine learning to suggest possible recommended health education modules that the client is asked to implement through the learning management system;

A care coordinator/supervisor/HUB staff or the CHR system may designate specific learning modules for the client/patient—The engagement is tracked and notifications made to all stakeholders;

The system may include engagement incentives for the client/patient and methodology from the CHR, sponsors or other contracts;

Specific forms, screenings, measurements can be designated for a client/patient to complete (with or without incentives); and Vital signs can be recorded or smart phone trackings enabled by the client/patient that are integrated with the CHR and their client record.

What has been described above includes examples of the claimed subject matter. It is, of course, not possible to describe every conceivable combination of components or methodologies for purposes of describing the claimed subject matter, but one of ordinary skill in the art can recognize that many further combinations and permutations of such matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

The foregoing method descriptions and the process flow diagrams are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor unit, but, in the alternative, the processor may be any conventional processor, controller, microcontroller, or state machine. A processor may also be implemented as a combination of computing devices, e.g., a combination of a DSP and a microprocessor unit, a plurality of microprocessor units, one or more microprocessor units in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored on or transmitted over as one or more instructions or code on a computer-readable medium. The steps of a method or algorithm disclosed herein may be embodied in a processor-executable software module, which may reside on a tangible, non-transitory computer-readable storage medium. Tangible, non-transitory computer-readable storage media may be any available media that may be accessed by a computer. By way of example, and not limitation, such non-transitory computer-readable media may comprise RAM, ROM, EEPROM, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of non-transitory computer-readable media. Additionally, the operations of a method or algorithm may reside as one or any combination or set of codes and/or instructions on a tangible, non-transitory machine readable medium and/or computer-readable medium, which may be incorporated into a computer program product.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

The following images of the software are for the purposes of displaying and illuminating one embodiment of the invention and should not be seen as limiting the scope of the invention solely to the images displayed.

What is claimed is:

1. A system for coordinating medical care comprising: i) a hub computing device which operates as a hub portal comprising a processor, a display and a non-transitory computer-readable storage medium containing a set of instructions encoded thereon, the instructions comprising: a data collection component, wherein the data collection component allows for a listing of clients or patients including client information and referral information, and a listing of medical, health and social service providers to be uploaded onto the hub portal by a hub portal user and for recording of a patient's community health records with various service providers through use of the system; a health bridge referral component which allows the hub portal user to receive a request for a patient referral from a service provider, to access the patient's account, to conduct a search of service providers through a search engine, to select a service provider and add the type of referral requested: a first monitoring component which allows the hub portal user to enter a patient's account for a referral and view information associated with the patient within the account and which allows the hub portal user to monitor electronic communications between the patient and a service provider for particular patient referrals; a patient account status component which allows the hub portal user to monitor a patient's status of treatment within a particular pathway and which allows the hub portal user the ability to close a patient's account upon completion of a patient's treatment or pathway; and an archiving component which allows a hub portal user to move a particular referral or pathway to a historic tab upon completion of a patient's treatment or pathway; a measure, process and data display component wherein data related to a patient's community health record is run through artificial intelligence learning processes to analyze the data and generate an output of recommendations for further pathway referrals and/or treatments and to analyze multiple patient data within a particular region and output data directed to health related trends within a particular region, wherein the measure, process and data display component further analyzes which pathways provide the most successful outcomes for individuals with certain conditions in a particular region, determines the factors that cause poor health outcomes within a community, determines which pathways are likely to provide the most successful outcomes for individuals having certain conditions in a particular region and provides pathway recommendations for individuals within a particular region; a plurality of client computing devices comprising: a processor, a display and a non-transitory computer-readable storage medium containing a set of instructions encoded thereon, the instructions comprising: a search engine component, wherein the search engine component returns a number of hits of medical, health or social service providers within a selected region upon a client user entering a query within the search engine; a messaging component which allows the client user to send an electronic message to an organization selected from a list of service providers obtained from the search engine query to request an appointment to obtain community services; a scheduling component which allows for appointments to be created between the patient and the service provider; a confirmation component which allows the service provider to confirm receipt of the appointment request or referral wherein the hub computing device is directly linked to the client devices and communicatively coupled to the client devices through a network connection.

2. The system of claim 1, further comprising an appointment feedback component which provides notice to a third party referring the patient for the appointment with the service provider that the appointment was kept.

3. The system of claim 2, further comprising a health record integration component which allows a patient's medical records or electronic health record with a medical service provider to be uploaded and merged with the patient's community health record established with various service providers through use of the system.

4. The system of claim 3, wherein the messaging component allows for multi-user, real-time communications between the patient and the service provider.

5. The system of claim 4, further comprising a second monitoring component which allows health care providers to monitor electronic communications between the patient and community service providers within the system.

6. The system of claim 5, further comprising a direct messaging component which allows patients to communicate with service providers confidentially in a secure environment within the system.

7. The system of claim 6, further comprising a tracking component wherein community health records are entered into a patient's account within the system through completed Pathway forms which tracks the outcomes performed by the service provider.

8. The system of claim 7, wherein the archiving component allows for recording and storing of patient community health records related to service visits, general patient records and general data entry related to the specific services provided.

9. The system of claim 8, further comprising an auto-invoicing component, wherein the auto-invoicing component works in conjunction with the archiving component to automatically generate bills for services provided to the patient.

10. The system of claim 9, wherein the auto-invoicing component is performance-based in that it takes into account a patient's successful completion of pathways with the service provider in generating bills.

11. The system of claim 1, further comprising a referral resource ranking component wherein the hub portal user and service providers are provided a curated list of referral resources that are ranked according to performance and curated and maintained by HUB operations.

12. The system of claim 11, wherein a specific standardized pathway is identified and assigned to the patient for each risk factor identified by the service provider.

13. The system of claim 12, wherein a reduction in risk is recorded and tracked by the completion of pathways.

14. The system of claim 13, wherein in the event that a pathway which is not completed or a desired outcome is not reached for a given patient, the pathway is closed by marking it "finished incomplete", and wherein the service provider documents the reasons why the pathway was not successfully completed and records this data within the patient account within the system.

15. The system of claim 14, wherein pathway incompletion data is monitored and tracked by the hub computing device and wherein the hub computing device compiles a list of reasons why pathways are "finished incomplete".

16. The system of claim 15, wherein the hub computing device conducts a community needs assessment.

17. The system of claim 16, wherein the hub portal user creates agreements with community-based organizations or agencies to delineate expectations around hiring, training and supervision of service providers employed with such community-based organizations or agencies.

18. The system of claim 17, wherein the hub portal user, service provider, community-based organization or agency designates specific learning modules or training videos for the patient to view within the system.

19. The system of claim 18, wherein patient engagement is tracked within the system and notifications concerning the patient's engagement is transmitted to all financial stakeholders.

* * * * *